(12) United States Patent
Morton

(10) Patent No.: US 9,158,030 B2
(45) Date of Patent: Oct. 13, 2015

(54) X-RAY TOMOGRAPHIC INSPECTION SYSTEM FOR THE IDENTIFICATION OF SPECIFIC TARGET ITEMS

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

(*) Notice: Subject to any disclaimer, the term of this patent is extended or adjusted under 35 U.S.C. 154(b) by 0 days.

(21) Appl. No.: 14/508,464

(22) Filed: Oct. 7, 2014

(65) Prior Publication Data

US 2015/0110240 A1   Apr. 23, 2015

Related U.S. Application Data

(60) Continuation of application No. 13/870,407, filed on Apr. 25, 2013, now Pat. No. 8,885,794, which is a continuation of application No. 12/788,083, filed on May 26, 2010, now Pat. No. 8,451,974, which is a (Continued)

(30) Foreign Application Priority Data

| Apr. 25, 2003 | (GB) | 0309371.3 |
| --- | --- | --- |
| Apr. 25, 2003 | (GB) | 0309374.7 |
| Apr. 25, 2003 | (GB) | 0309379.6 |
| Apr. 25, 2003 | (GB) | 0309383.8 |
| Apr. 25, 2003 | (GB) | 0309385.3 |
| Apr. 25, 2003 | (GB) | 0309387.9 |
| Dec. 16, 2005 | (GB) | 0525593.0 |
| Jul. 15, 2008 | (GB) | 0812864.7 |
| Feb. 25, 2009 | (GB) | 0903198.0 |

(51) Int. Cl.
| A61B 6/00 | (2006.01) |
| --- | --- |
| G01V 5/00 | (2006.01) |
| G01N 23/04 | (2006.01) |
| H01J 35/04 | (2006.01) |

(Continued)

(52) U.S. Cl.
CPC .............. *G01V 5/0033* (2013.01); *G01N 23/04* (2013.01); *G01N 23/046* (2013.01); *G01N 23/203* (2013.01); *G01N 24/084* (2013.01); *G01V 5/005* (2013.01); *H01J 35/045* (2013.01); *A61B 6/027* (2013.01); *A61B 6/032* (2013.01); *A61B 6/4028* (2013.01); *A61B 6/4035* (2013.01); *A61B 6/4241* (2013.01); *A61B 6/4488* (2013.01); *A61B 6/482* (2013.01); *A61B 6/505* (2013.01); *G01N 2223/419* (2013.01)

(58) Field of Classification Search
CPC ... G01N 23/04; G01N 23/046; G01N 23/203; G01N 24/084; H01J 35/045; G01V 5/005; G01V 5/0033; A61B 6/032; A61B 6/035; A61B 6/4241

See application file for complete search history.

(56) References Cited

U.S. PATENT DOCUMENTS

2005/0104603 A1* 5/2005 Peschmann et al. .......... 324/637

*Primary Examiner* — Courtney Thomas
(74) *Attorney, Agent, or Firm* — Novel IP

(57) ABSTRACT

The present invention provides for an improved scanning process with a stationary X-ray source arranged to generate X-rays from a plurality of X-ray source positions around a scanning region, a first set of detectors arranged to detect X-rays transmitted through the scanning region, and at least one processor arranged to process outputs from the first set of detectors to generate tomographic image data. The X-ray screening system is used in combination with other screening technologies, such as NQR-based screening, X-ray diffraction based screening, X-ray back-scatter based screening, or Trace Detection based screening.

20 Claims, 19 Drawing Sheets

Related U.S. Application Data continuation-in-part of application No. 12/371,853, filed on Feb. 16, 2009, now Pat. No. 7,903,789, which is a continuation of application No. 10/554,975, filed as application No. PCT/GB2004/001741 on Apr. 23, 2004, now Pat. No. 7,512,215, said application No. 12/788,083 is a continuation-in-part of application No. 12/651,479, filed on Jan. 3, 2010, now abandoned, which is a continuation of application No. 10/554,654, filed as application No. PCT/GB2004/001731 on Apr. 23, 2004, now Pat. No. 7,664,230, said application No. 12/788,083 is a continuation-in-part of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, said application No. 12/788,083 is a continuation-in-part of application No. 12/758,764, filed on Apr. 12, 2010, now Pat. No. 7,929,663, which is a continuation of application No. 12/211,219, filed on Sep. 16, 2008, now Pat. No. 7,724,868, which is a continuation of application No. 10/554,655, filed as application No. PCT/GB2004/001751 on Apr. 23, 2004, now Pat. No. 7,440,543, said application No. 12/788,083 is a continuation-in-part of application No. 12/697,073, filed on Jan. 29, 2010, now Pat. No. 8,085,897, which is a continuation of application No. 10/554,570, filed as application No. PCT/GB2004/001747 on Apr. 23, 2004, now Pat. No. 7,684,538, said application No. 12/788,083 is a continuation-in-part of application No. 12/097,422, filed as application No. PCT/GB2006/004684 on Dec. 15, 2006, now Pat. No. 7,876,879, said application No. 12/788,083 is a continuation-in-part of application No. 12/142,005, filed on Jun. 19, 2008, now Pat. No. 8,135,110, and a continuation-in-part of application No. 12/478,757, filed on Jun. 4, 2009, now Pat. No. 8,094,784, which is a continuation-in-part of application No. 12/364,067, filed on Feb. 2, 2009, now abandoned, which is a continuation-in-part of application No. 12/033,035, filed on Feb. 19, 2008, now Pat. No. 7,505,563, said application No. 12/788,083 is a continuation-in-part of application No. 12/712,476, filed on Feb. 25, 2010, now Pat. No. 8,243,876, said application No. 12/788,083 is a continuation-in-part of application No. 12/505,659, filed on Jul. 20, 2009, now Pat. No. 8,138,770, which is a continuation of application No. 12/175,599, filed on Jul. 18, 2008, now Pat. No. 7,579,845, which is a division of application No. 10/952,665, filed on Sep. 29, 2004, now Pat. No. 7,417,440, which is a continuation-in-part of application No. 10/662,778, filed on Sep. 15, 2003, now abandoned, said application No. 12/788,083 is a continuation-in-part of application No. 12/485,897, filed on Jun. 16, 2009, now abandoned, which is a continuation of application No. 10/554,656, filed as application No. PCT/GB2004/001729 on Apr. 23, 2004, now Pat. No. 7,564,939.

(60) Provisional application No. 61/181,070, filed on May 26, 2009, provisional application No. 61/155,572, filed on Feb. 26, 2009.

(51) Int. Cl.
*G01N 23/203* (2006.01)
*G01N 24/08* (2006.01)
*A61B 6/02* (2006.01)
*A61B 6/03* (2006.01)

X-RAY TOMOGRAPHIC INSPECTION SYSTEM FOR THE IDENTIFICATION OF SPECIFIC TARGET ITEMS

CROSS-REFERENCE TO RELATED APPLICATIONS

The present application is a continuation of U.S. patent application Ser. No. 13/870,407, filed on Apr. 25, 2013, which is a continuation of U.S. patent application Ser. No. 12/788,083, filed on May 26, 2010, now U.S. Pat. No. 8,451,974, issued on May 28, 2013, which relies on U.S. Provisional Patent Application No. 61/181,070 filed on May 26, 2009, for priority.

The '083 application is a continuation-in-part of U.S. patent application Ser. No. 12/485,897, filed on Jun. 16, 2009, which is a continuation of U.S. patent application Ser. No. 10/554,656, filed on Oct. 25, 2005, and now issued U.S. Pat. No. 7,564,939, which is a 371 national stage application of PCT/GB04/01729, filed on Apr. 23, 2004 and which, in turn, relies on Great Britain Application No. 0309387.9, filed on Apr. 25, 2003, for priority.

The '083 application is also a continuation-in-part of U.S. patent application Ser. No. 12/371,853, filed on Feb. 16, 2009, which is a continuation of U.S. patent application Ser. No. 10/554,975, filed on Oct. 25, 2005, and now issued U.S. Pat. No. 7,512,215, which is a 371 national stage application of PCT/GB2004/01741, filed on Apr. 23, 2004 and which, in turn, relies on Great Britain Application Number 0309383.8, filed on Apr. 25, 2003, for priority.

The '083 application is also a continuation-in-part of U.S. patent application Ser. No. 12/651,479, filed on Jan. 3, 2010, which is a continuation of U.S. patent application Ser. No. 10/554,654, filed on Oct. 25, 2005, and now issued U.S. Pat. No. 7,664,230, which is a 371 national stage application of PCT/GB2004/001731, filed on Apr. 23, 2004 and which, in turn, relies on Great Britain Patent Application Number 0309371.3, filed on Apr. 25, 2003, for priority.

The '083 application is also a continuation-in-part of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority.

The '083 application is also a continuation-in-part of U.S. patent application Ser. No. 12/758,764, filed on Apr. 12, 2010, which is a continuation of U.S. patent application Ser. No. 12/211,219, filed on Sep. 16, 2008, and now issued U.S. Pat. No. 7,724,868, which is a continuation of U.S. patent Ser. No. 10/554,655, filed on Oct. 25, 2005, and now issued U.S. Pat. No. 7,440,543, which is a 371 national stage application of PCT/GB2004/001751, filed on Apr. 23, 2004, and which, in turn, relies on Great Britain Patent Application Number 0309385.3, filed on Apr. 25, 2003, for priority.

The '083 application is also a continuation-in-part of U.S. patent application Ser. No. 12/697,073, filed on Jan. 29, 2010, which is a continuation of U.S. patent application Ser. No. 10/554,570, filed on Oct. 25, 2005, and now issued U.S. Pat. No. 7,684,538, which is a 371 national stage application of PCT/GB2004/001747, filed on Apr. 23, 2004, and which, in turn, relies on Great Britain Patent Application Number 0309379.6, filed on Apr. 25, 2003, for priority.

The '083 application is also a continuation-in-part of U.S. patent application Ser. No. 12/097,422, filed on Jun. 13, 2008, and U.S. patent application Ser. No. 12/142,005, filed on Jun. 19, 2008, both of which are 371 national stage applications of PCT/GB2006/004684, filed on Dec. 15, 2006, which, in turn, relies on Great Britain Patent Application Number 0525593.0, filed on Dec. 16, 2005, for priority.

The '083 application is also a continuation-in-part of U.S. patent application Ser. No. 12/478,757, filed on Jun. 4, 2009, which is a continuation of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority. In addition, U.S. patent application number relies on Great Britain Patent Application Number 0812864.7, filed on Jul. 15, 2008, for priority.

The '083 application is also a continuation-in part of U.S. patent application Ser. No. 12/712,476, filed on Feb. 25, 2010, which relies on U.S. Provisional Patent Application No. 61/155,572 filed on Feb. 26, 2009 and Great Britain Patent Application No. 0903198.0 filed on Feb. 25, 2009, for priority.

The '083 application is also a continuation-in-part of U.S. patent application Ser. No. 12/505,659, filed on Jul. 20, 2009, which is a continuation of U.S. patent application Ser. No. 12/175,599, filed on Jul. 18, 2008, which, in turn, is a continuation of U.S. patent application Ser. No. 10/952,665, filed on Sep. 29, 2004.

Each of the aforementioned PCT, foreign, and U.S. applications, and any applications related thereto, is herein incorporated by reference in their entirety.

FIELD OF THE INVENTION

The present invention relates to X-ray scanning and, particularly to the security screening of baggage and packages for contraband and suspicious objects, such as sharp objects, knives, nuclear materials, tobacco, currency, narcotics, and liquids.

BACKGROUND OF THE INVENTION

X-ray computed tomography (CT) scanners have been used in security screening in airports for several years. A conventional system comprises an X-ray tube that is rotated about an axis with an arcuate X-ray detector that is rotated at the same speed around the same axis. The conveyor belt on which the baggage is carried is placed within a suitable aperture around the central axis of rotation, and moved along the axis as the tube is rotated. A fan-beam of X-radiation passes from the source through the object to be inspected to the X-ray detector array.

The X-ray detector array records the intensity of X-rays passed through the object to be inspected at several locations along its length. One set of projection data is recorded at each of a number of source angles. From these recorded X-ray intensities, it is possible to form a tomographic (cross-sectional) image, typically by means of a filtered back projection algorithm. In order to produce an accurate tomographic image of an object, such as a bag or package, it can be shown that there is a requirement that the X-ray source pass through every plane through the object. In the arrangement described above, this is achieved by the rotational scanning of the X-ray source, and the longitudinal motion of the conveyor on which the object is carried.

In this type of system the rate at which X-ray tomographic scans can be collected is dependent on the speed of rotation of the gantry that holds the X-ray source and detector array. In a modern CT gantry, the entire tube-detector assembly and gantry will complete two to four revolutions per second. This allows up to four or eight tomographic scans to be collected per second respectively.

As the state-of-the-art has developed, the single ring of X-ray detectors has been replaced by multiple rings of detectors. This allows many slices (typically 8) to be scanned simultaneously and reconstructed using filtered back projection methods adapted from the single scan machines. With a continuous movement of the conveyor through the imaging system, the source describes a helical scanning motion about the object. This allows a more sophisticated cone-beam image reconstruction method to be applied that can in principle offer a more accurate volume image reconstruction.

In a further development, swept electron beam scanners have been demonstrated in medical applications whereby the mechanical scanning motion of the X-ray source and detectors is eliminated, being replaced by a continuous ring (or rings) of X-ray detectors that surround the object under inspection with a moving X-ray source being generated as a result of sweeping an electron beam around an arcuate anode. This allows images to be obtained more rapidly than in conventional scanners. However, because the electron source lies on the axis of rotation, such swept beam scanners are not compatible with conveyor systems which themselves pass close, and parallel, to the axis of rotation.

The present invention provides an X-ray scanning system for inspecting items, the system comprising an X-ray source extending around a scanning volume, and defining a plurality of source points from which X-rays can be directed through the scanning volume, an X-ray detector array also extending around the scanning volume and arranged to detect X-rays from the source points which have passed through the scanning volume and produce output signals dependent on the detected X-rays, and a conveyor arranged to convey the items through the scanning volume.

The present invention further provides a networked inspection system comprising an X-ray scanning system, a workstation and connection means arranged to connect the scanning system to the workstation, the scanning system comprising an X-ray source extending around a scanning volume, and defining a plurality of source points from which X-rays can be directed through the scanning volume, an X-ray detector array also extending around the scanning volume and arranged to detect X-rays from the source points which have passed through the scanning volume and produce output signals dependent on the detected X-rays, and a conveyor arranged to convey the items through the scanning volume.

The present invention further provides a sorting system for sorting items, the system comprising a tomographic scanner arranged to scan a plurality of scanning regions of each item thereby to produce a scanner output, analyzing means arranged to analyze the scanner output and allocate each item to one of a plurality of categories at least partly on the basis of the scanner output, and sorting means arranged to sort items at least partly on the basis of the categories to which they have been allocated.

The present invention further provides an X-ray scanning system comprising an X-ray source arranged to generate X-rays from a plurality of X-ray source positions around a scanning region, a first set of detectors arranged to detect X-rays transmitted through the scanning region, a second set of detectors arranged to detect X-rays scattered within the scanning region, and processing means arranged to process outputs from the first set of detectors to generate image data which defines an image of the scanning region, to analyze the image data to identify an object within the image, and to process the outputs from the second set of detectors to generate scattering data, and to associate parts of the scattering data with the object.

The present invention further provides a data collecting system for collecting data from an X-ray scanner, the system comprising a memory having a plurality of areas each being associated with a respective area of an image, data input means arranged to receive input data from a plurality of X-ray detectors in a predetermined sequence, processing means arranged to generate from the input data X-ray transmission data and X-ray scattering data associated with each of the areas of the image, and to store the X-ray transmission data and the X-ray scattering data in the appropriate memory areas.

The present invention further provides an X-ray scanning system comprising a scanner arranged to scan an object to generate scanning data defining a tomographic X-ray image of the object, and processing means arranged to analyze the scanning data to extract at least one parameter of the image data and to allocate the object to one of a plurality of categories on the basis of the at least one parameter.

Furthermore, there exists a requirement to screen baggage and cargo items for the presence of explosive materials and explosive devices. Such a scan typically must be performed at a high speed, as measured in baggage and cargo item throughput, but with a high standard of detection performance and a reduced false alarm level. False alarms that are generated require further inspection, which may involve reconciliation of the baggage or cargo item with the owner of that item prior to a manual search. Such processes are expensive and time consuming.

There is also a need to combine a high throughput tomography system with a secondary system capable of specifically detecting explosive devices. One or more two-dimensional X-ray images are acquired at one or more various projection angles at high speed (typically with a conveyor speed of 0.5 m/s). An automated algorithm analyzes these images for the presence of a likely threat material or device. In the event that such a device or material is found, the item of baggage of cargo is routed to a second system which can form one or more tomographic slice reconstructions through the item. Due to the slow speed of known systems, only a small fraction of baggage and cargo items can be screened in this way. The tomographic image or images is/are then analyzed by an automated explosives detection algorithm. Frequently, the algorithm will raise an alarm on the baggage or cargo item and the image data must then be viewed by a human operator. The fraction of items that continue to raise an alarm at this point are then subject to reconciliation and human search.

SUMMARY OF THE INVENTION

The present invention is directed toward a system for identifying objects in a container, such as cargo or luggage, comprising a first screening system and second screening system. The first screening system comprises a stationary X-ray source arranged to generate X-rays from a plurality of X-ray source positions around a scanning region; a first set of detectors arranged to detect X-rays transmitted through the scanning region; a second set of detectors arranged to detect X-rays scattered within the scanning region; at least one processor configured to process data output from the first set of detectors and generate at least one tomographic image and to process data output from the second set of detectors to generate scatter image data; and a second screening system comprising at least one of a NQR-based screening system, X-ray diffraction based screening system, X-ray back-scatter based screening system, or trace detection based screening system.

Optionally, the at least one processor outputs data indicative of a suspect object in the container. A suspect object is any object that is the subject of interest by persons operating the X-ray scanning system, such as threat objects, illegal objects, contraband, weapons, narcotics, nuclear materials, currency, tobacco, knives, bombs, and other such items. The at least one processor outputs a signal indicating said container should be subject to the second screening system only if the first screening system identifies a suspect object in the container. The at least one processor outputs a signal indicating said container should not be subject to the second screening system only if the first screening system does not identify a suspect object in the container. The second screening system outputs a signal indicative of whether a suspect object exists in the container and said output of the second screening system, said tomographic image data, and said scatter image data are used to determine if the suspect object is illegal.

The first screening system operates in parallel with said second screening system. The first screening system operates serially with respect to said second screening system. The first screening system analyzes at least one of the tomographic image data or scatter image data to determine a type of material of an object in the enclosure. The second screening system conducts a nuclear quadrupole measurement based on the type of material determined by the first screening system. The second screening system conducts an X-ray diffraction based screening based on the tomographic image generated by the first screening system. The stationary X-ray source is an electronically scanned X-ray source.

In another embodiment, the present invention comprises a system for identifying objects in a container that comprises a first screening system and a conveyor system that moves a container to a second screening system. The conveyor can be any motive mechanism, including a conventional conveyor belt, carts, manually manipulated pallets, lifts, or other structures. The first screening system comprises a stationary X-ray source arranged to generate X-rays from a plurality of X-ray source positions around a scanning region; a first set of detectors arranged to detect X-rays transmitted through the scanning region; at least one processor configured to process data output from the first set of detectors and generate at least one tomographic image; and a conveying system to move said container from the first screening system to a second screening system, wherein the second screening system comprises at least one of a NQR-based screening system, X-ray diffraction based screening system, X-ray back-scatter based screening system, or trace detection based screening system.

Optionally, the at least one processor outputs data indicative of a suspect object in the container. The at least one processor outputs a signal indicating said container should be subject to the second screening system only if the first screening system identifies a suspect object in the container. The second screening system outputs a signal indicative of whether a suspect object exists in the container and said output of the second screening system and said tomographic image data are used to determine if the suspect object is a threat. The first screening system operates in parallel with said second screening system. The first screening system operates serially with respect to said second screening system. The first screening system analyzes the tomographic image data to determine a type of material of an object in the enclosure. The second screening system conducts a nuclear quadrupole measurement based on the type of material determined by the first screening system. The second screening system conducts an X-ray diffraction based screening based on the tomographic image generated by the first screening system.

BRIEF DESCRIPTION OF THE DRAWINGS

Embodiments of the present invention will now be described by way of example only with reference to the accompanying drawings in which.

DETAILED DESCRIPTION OF THE INVENTION

Figure 1:
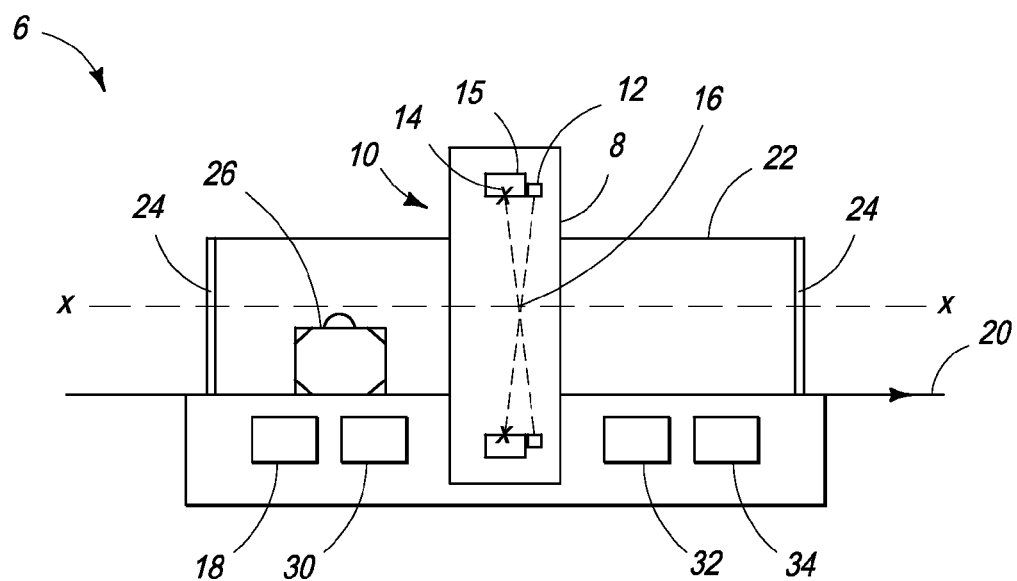
FIG. 1 is a longitudinal section of a real time tomography security scanning system according to a first embodiment of the invention.
Figure 2:
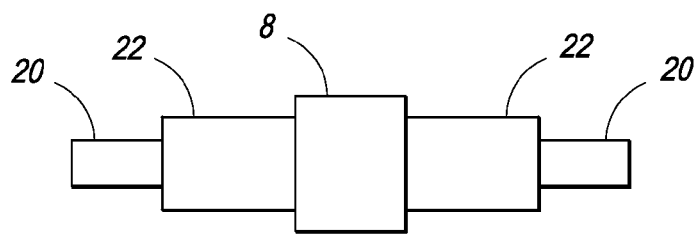
FIG. 2 is a plan view of the system of FIG. 1.
Figure 3:
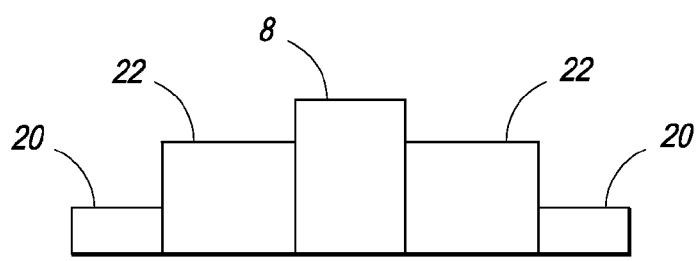
FIG. 3 is a schematic side view of the system of FIG. 1.

Referring to FIGS. 1 to 3, a concourse baggage scanning system 6 comprises a scanning unit 8 comprising a multi-focus X-ray source 10 and X-ray detector array 12. The source 10 comprises a large number of source points 14 in respective spaced locations on the source, and arranged in a full 360.degree. circular array around the axis X-X of the system. It will be appreciated that arrays covering less than the full 360.degree. angle can also be used.

Figure 1A:
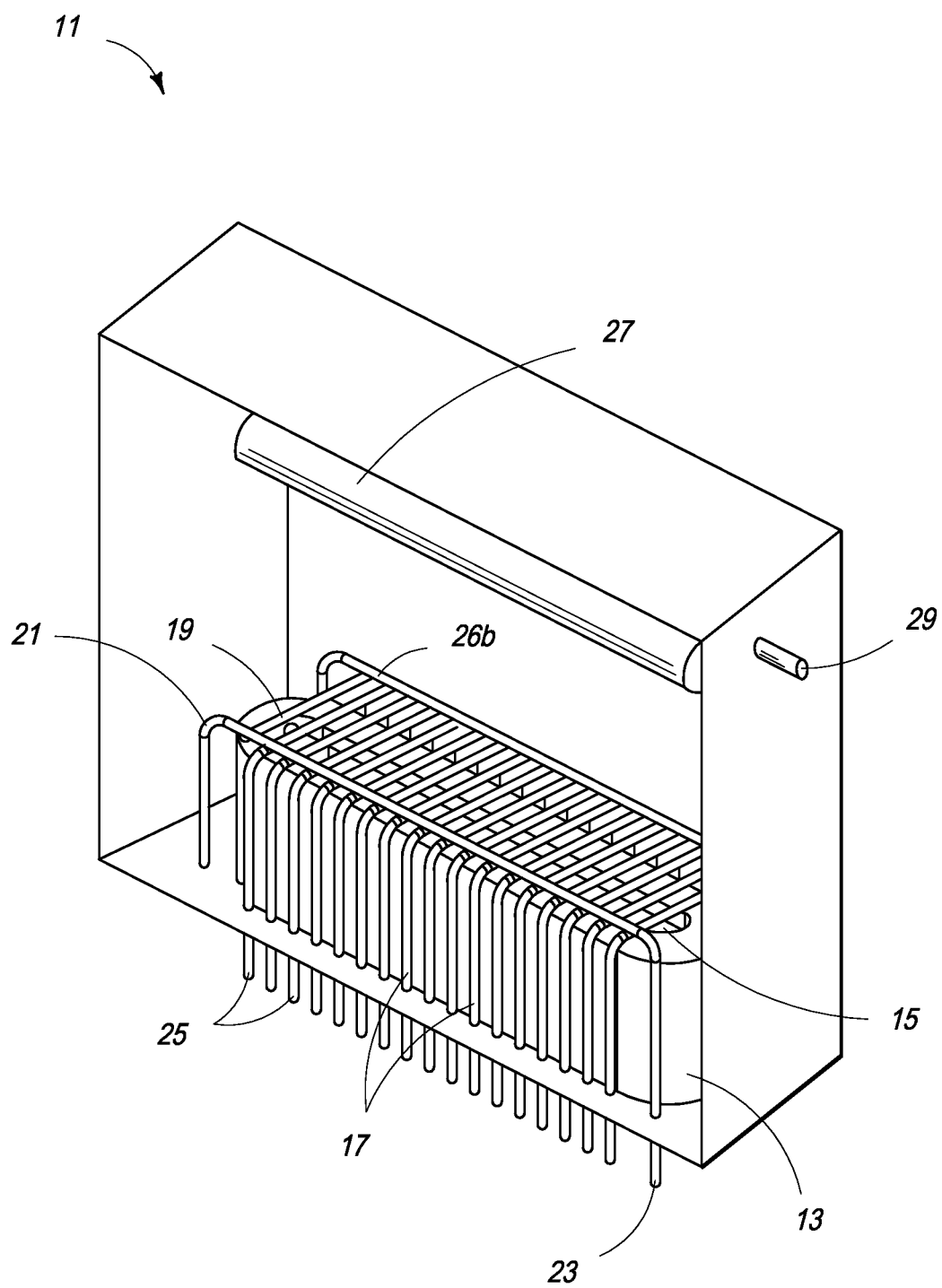
FIG. 1a is a perspective view of an X-ray source of the system of FIG. 1.

Referring to FIG. 1a, the X-ray source 10 is made up of a number of source units 11 which are spaced around the scanning region 16 in a substantially circular arrangement, in a plane perpendicular to the direction of movement of the conveyor. Each source unit 11 comprises a conductive metal suppressor 13 having two sides and an emitter element 15 extending along between the suppressor sides. A number of grid elements in the form of grid wires 17 are supported above the suppressor 13 perpendicular to the emitter element 15. A number of focusing elements in the form of focusing wires 19 are supported in another plane on the opposite side of the grid wires to the emitter element. The focusing wires 19 are parallel to the grid wires 17 and spaced apart from each other with the same spacing as the grid wires, each focusing wire 19 being aligned with a respective one of the grid wires 17.

The focusing wires 19 are supported on two support rails 21 which extend parallel to the emitter element 15, and are spaced from the suppressor 13. The support rails 21 are electrically conducting so that all of the focusing wires 19 are electrically connected together. One of the support rails 21 is connected to a connector 23 to provide an electrical connection for the focusing wires 19. Each of the grid wires 17 extends down one side of the suppressor 12 and is connected to a respective electrical connector 25 which provide separate electrical connections for each of the grid wires 17.

An anode 27 is supported above the grid wires 17 and focusing wires 19. The anode 27 is formed as a rod, typically of copper with tungsten or silver plating, and extends parallel to the emitter element 15. The grid and focusing wires 17, 19 therefore extend between the emitter element 15 and the anode 27. An electrical connector 29 provides an electrical connection to the anode 27.

The grid wires 17 are all connected to a negative potential, apart from two which are connected to a positive potential. These positive grid wires extract a beam of electrons from an area of the emitter element 15 and, with focusing by the focusing wires 19, direct the electron beam at a point on the anode 27, which forms the X-ray source point for that pair of grid wires. The potential of the grid wires can therefore be switched to select which pair of grid wires is active at any one time, and therefore to select which point on the anode 27 is the active X-ray source point at any time.

The source 10 can therefore be controlled to produce X-rays from each of the source points 14 in each of the source units 11 individually and, referring back to FIG. 1, X-rays from each source point 14 are directed inwards through the scanning region 16 within the circular source 10. The source 10 is controlled by a control unit 18 which controls the electrical potentials applied to the grid wires 17 and hence controls the emission of X-rays from each of the source points 14. Other suitable X-ray source designs are described in WO 2004/097889.

The multi-focus X-ray source 10 allows the electronic control circuit 18 to be used to select which of the many individual X-ray source points 14 within the multi-focus X-ray source is active at any moment in time. Hence, by electronically scanning the multi-focus X-ray tube, the illusion of X-ray source motion is created with no mechanical parts physically moving. In this case, the angular velocity of source rotation can be increased to levels that simply cannot be achieved when using conventional rotating X-ray tube assemblies. This rapid rotational scanning translates into an equivalently speeded up data acquisition process and subsequently fast image reconstruction.

The detector array 12 is also circular and arranged around the axis X-X in a position that is slightly offset in the axial direction from the source 10. The source 10 is arranged to direct the X-rays it produces through the scanning region 16 towards the detector array 12 on the opposite side of the scanning region. The paths 18 of the X-ray beams therefore pass through the scanning region 16 in a direction that is substantially, or almost, perpendicular to the scanner axis X-X, crossing each other near to the axis. The volume of the scanning region that is scanned and imaged is therefore in the form of a thin slice perpendicular to the scanner axis. The source is scanned so that each source point emits X-rays for a respective period, the emitting periods being arranged in a predetermined order. As each source point 14 emits X-rays, the signals from the detectors 12, which are dependent on the intensity of the X-rays incident on the detector, are produced, and the intensity data that the signals provide are recorded in memory. When the source has completed its scan the detector signals can be processed to form an image of the scanned volume.

A conveyor belt 20 moves through the imaging volume, from left to right, as seen in FIG. 1, parallel to the axis X-X of the scanner. X-ray scatter shields 22 are located around the conveyor belt 20 upstream and downstream of the main X-ray system to prevent operator dose due to scattered X-rays. The X-ray scatter shields 22 include lead rubber strip curtains 24 at their open ends such that the item 26 under inspection is dragged through one curtain on entering, and one on leaving, the inspection region. In the integrated system shown, the main electronic control system 18, a processing system 30, a power supply 32 and cooling racks 34 are shown mounted underneath the conveyor 20. The conveyor 20 is arranged to be operated normally with a continuous scanning movement at constant conveyor speed, and typically has a carbon-fiber frame assembly within the imaging volume.

Figure 4:
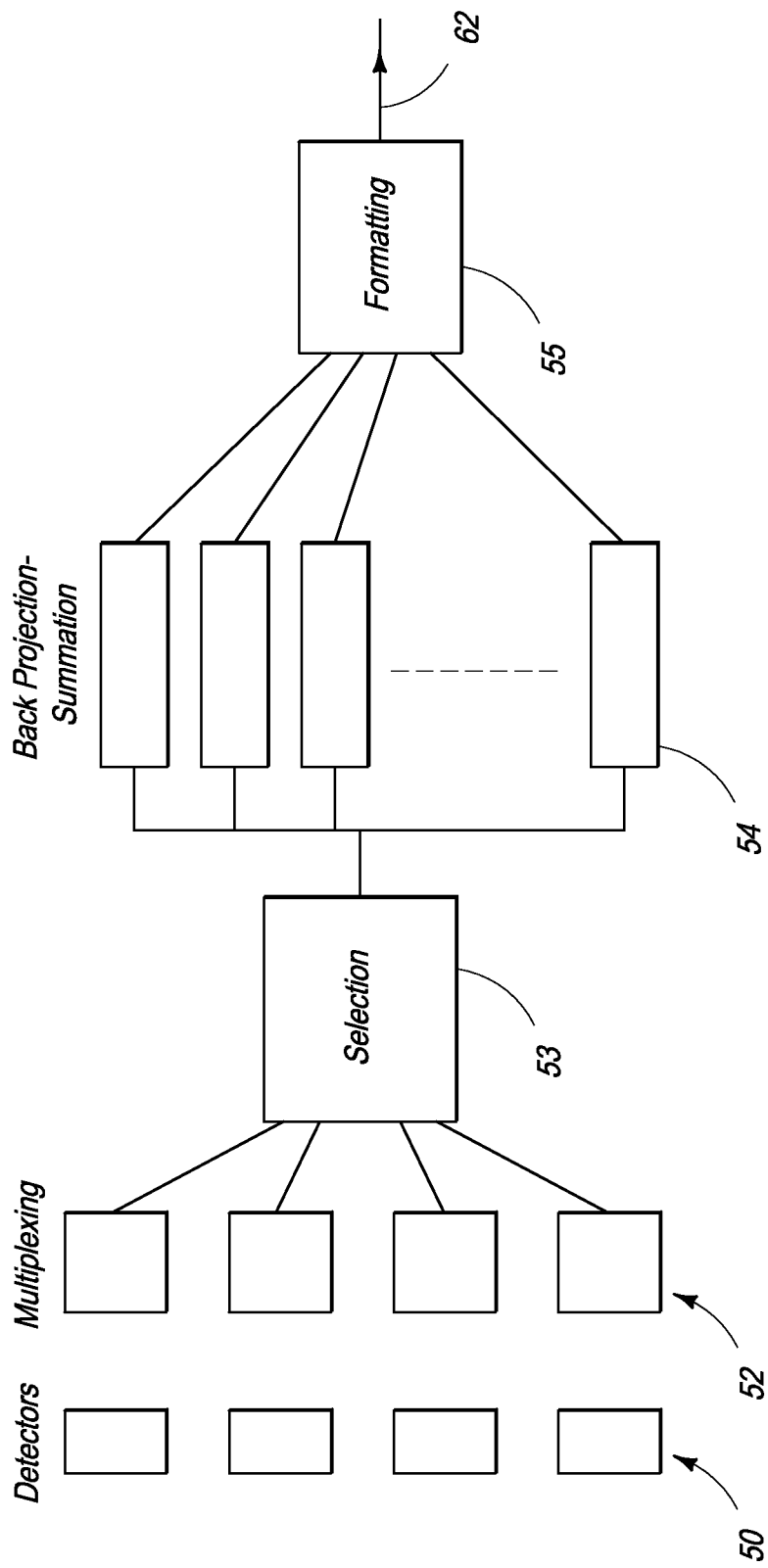
FIG. 4 is a schematic diagram of a data acquisition system forming part of the system of FIG. 1.

Referring to FIG. 4 the processing system 30 includes an electronic data acquisition system and real-time image reconstruction system. The X-ray detector array 12 comprises banks of individual X-ray detectors 50 configured in a simple linear pattern (e.g. 1.times.16). Multiple ring patterns (e.g. 8.times.16) are also possible. Each detector 50 outputs a signal dependent on the intensity of the X-rays it detects. A multiplexing block 52 multiplexes the output data signals from each of the input X-ray detectors 50, performs data filtering, gain and offset corrections and formats the data into a high-speed serial stream. A selection block 53 takes input from all of the multiplexing blocks 52 and selects just the part of the entire X-ray data that is required for the image reconstruction. The selection block 53 also determines the unattenuated X-ray beam intensity, Io, for the appropriate X-ray source point (which will vary for every X-ray source point within the multi-focus X-ray tube), processes the X-ray intensity data, Ix, from the multiplexing block 52 by forming the result $\log_o(Ix/Io)$ and then convolves this with a suitable 1-D filter. The resulting projection data is recorded as a sinogram, in which the data is arranged in an array with pixel number along one axis, in this case horizontally, and source angle along another axis, in this case vertically.

Data is then passed from the selection block 53 in parallel to a set of back projection-summation processor elements 54. The processor elements 54 are mapped into hardware, using look-up tables with pre-calculated coefficients to select the necessary convolved X-ray data and weighting factors for fast back projection and summation. A formatting block 55 takes the data representing individual reconstructed image tiles from the multiple processor elements 54 and formats the final output image data to a form suitable for generating a suitably formatted three dimensional image on a display screen. This output can be generated fast enough for the images to be generated in real time, for viewing in real time or off-line, hence the system is termed a real time tomography (RTT) system.

In this embodiment the multiplexing block 52 is coded in software, the selection block 53 and formatting block 55 are both coded in firmware, and the processor elements mapped in hardware. However, each of these components could be either hardware or software depending on the requirements of the particular system.

Figure 5:
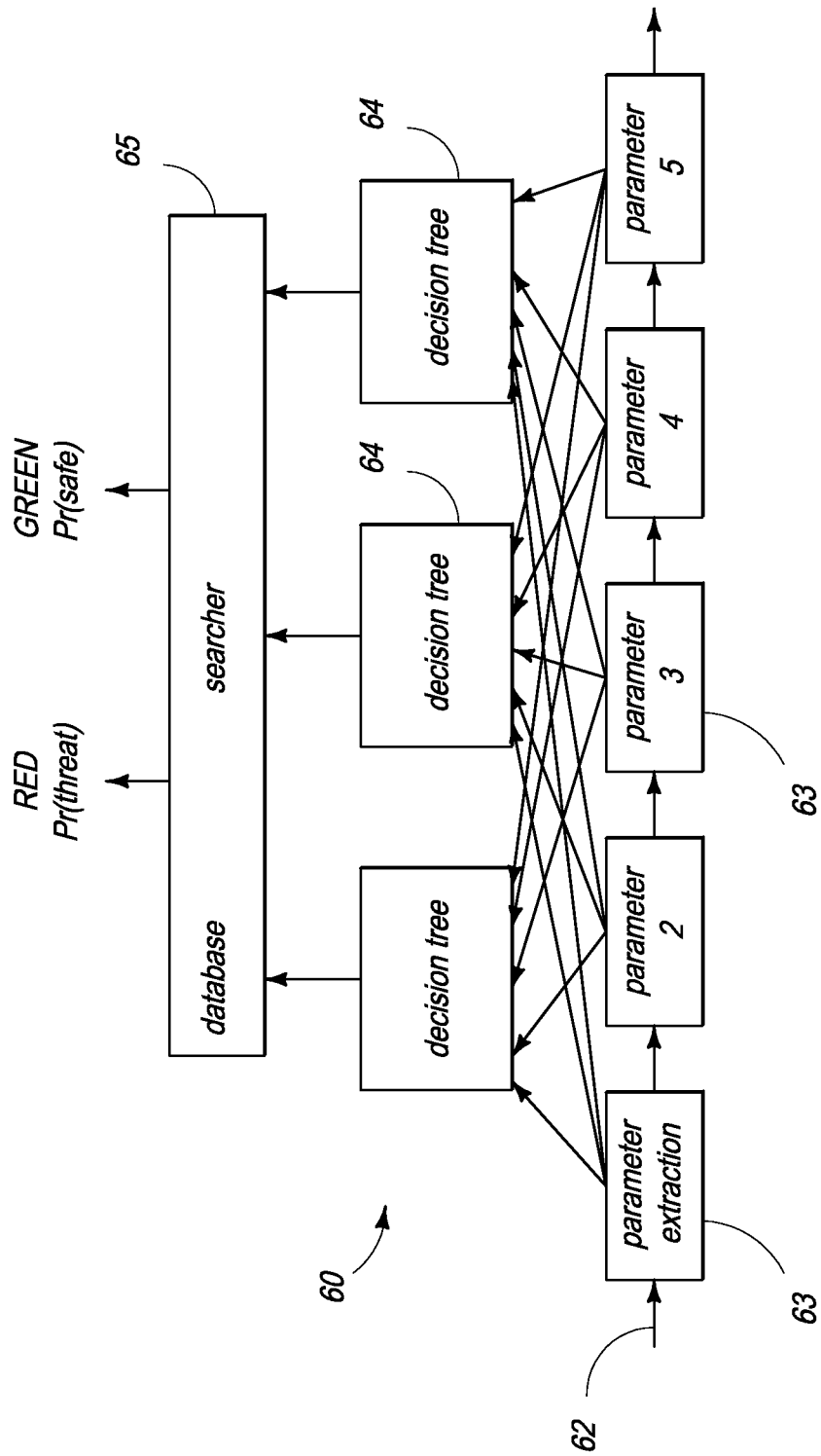
FIG. 5 is a schematic diagram of a threat detection system forming part of the system of FIG. 1.

Referring to FIG. 5 each of the final output images for each baggage item is then processed by a threat detection processor 60 within the processing system 30 which is arranged to determine whether the imaged baggage item represents a threat. In the threat detection processor 60, input X-ray tomographic image data 62 is passed in to a set of low-level parameter extractors 63 (level 1). The parameter extractors 63 identify features in the image such as areas of constant grey level, texture and statistics. Some of the extractors work on the data for individual 2 dimensional images or slices, some work on the 3 dimensional images, and some work on the sinogram data. Where possible, each extractor works in parallel on the same set of input data, and each extractor is arranged to perform a different processing operation and to determine a different parameter. At the end of the processing, the parameters determined by the parameter extractors 63 are passed up to a set of decision trees 64 (level 2). Details of the parameters extracted are given below. The decision trees 64 each take a number (typically all) of the low level parameters and construct respective higher level information, such as information regarding contiguous volumes, with associated statistics. At the top level (level 3), a database searcher 65 maps the higher level parameters produced at level 2 into a 'red' probability Pr(threat) of there being a threat present and a 'green' probability Pr(safe) of the item under inspection being safe. These probabilities are used by the processing system 30 to allocate the scanned item to an appropriate safety category, and to produce an automatic sorting control output. This automatic sorting control output can be either a first 'green' output indicating that the item is allocated to a clear category, a second 'red' output indicating that the item is allocated to a 'not clear' category, or a third 'amber' output indicating that the automatic sorting cannot be carried out with sufficient reliability to allocated the item to the 'clear' or the 'not clear' category. Specifically if Pr(safe) is above a predetermined value, (or Pr(threat) is below a predetermined value) then the automatic sorting output will be produced having a first signal form, indicating that the item should be allocated to the green channel. If Pr(threat) is above a predetermined value, (or Pr(safe) is below a predetermined value) then the automatic sorting output will be produced having a second signal form, indicating that the item should be allocated to the red channel. If Pr(threat) (or Pr(safe)) is between the two predetermined values, then the automatic sorting output is produced having a third signal form, indicating that the item cannot be allocated to either the red or green channel. The probabilities can also be output as further output signals.

The parameters that will be determined by the parameter extractors 63 generally relate to statistical analysis of pixels within separate regions of the 2-dimensional or 3-dimensional image. In order to identify separate regions in the image a statistical edge detection method is used. This starts at a pixel and then checks whether adjacent pixels are part of the same region, moving outwards as the region grows. At each step an average intensity of the region is determined, by calculating the mean intensity of the pixels within the region, and the intensity of the next pixel adjacent to the region is compared to that mean value, to determine whether it is close enough to it for the pixel to be added to the region. In this case the standard deviation of the pixel intensity within the region is determined, and if the intensity of the new pixel is within the standard deviation, then it is added to the region. If it is not, then it is not added to the region, and this defines the edge of the region as being the boundary between pixels in the region and pixels that have been checked and not added to the region.

Once the image has been divided into regions, then parameters of the region can be measured. One such parameter is a measure of the variance of the pixel intensity within the region. If this is high this might be indicative of a lumpy material, which might for example be found in a home-made bomb, while if the variance is low this would be indicative of a uniform material such as a liquid.

Another parameter that is measured is the skewedness of the distribution of pixel value within the region, which is determined by measuring the skewedness of a histogram of pixel values. A Gaussian, i.e. non-skewed, distribution indicates that the material within the region is uniform, whereas a more highly skewed distribution indicates non-uniformities in the region.

As described above, these low-level parameters are passed up to the decision trees 64, where higher level information is constructed and higher level parameters are determined. One such higher level parameter is the ratio of the surface area to the volume of the identified region. Another is a measure of similarity, in this case cross-correlation, between the shape of the region and template shapes stored in the system. The template shapes are arranged to correspond to the shape of items that pose a security threat, such as guns or detonators. These high level parameters are used as described above to determine a level if threat posed by the imaged object.

Figure 6:
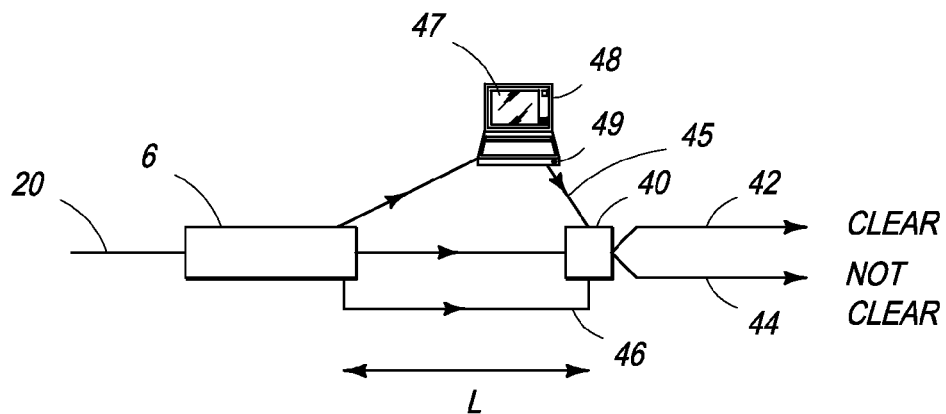
FIG. 6 is a schematic diagram of a baggage sorting system according to an embodiment of the invention including the scanning system of FIG. 1.

Referring to FIG. 6 an in-line real time tomography baggage sorting system comprises the scanning system 6 of FIG. 1 with the conveyor 20 passing through it. Downstream of the scanning system 6 a sorting device 40 is arranged to receive articles of baggage from the conveyor 20 and move them onto either a clear or 'green' channel conveyor 42 or a not clear or 'red' channel conveyor 44. The sorting device 40 is controlled by the automatic sorting output signals via a control line 46 from the processing system 30, which are indicative of the decision of the processing system 30 as to whether the item is clear or not, and also by signals from a workstation 48 to which it is connected via line 45. The images from the scanning system 6 and signals from the processing system 30, indicative of the red and green probabilities and the nominal decision of the processing system 30, are also fed to the workstation 48. The workstation is arranged to display the images on a screen 47 so that they can be viewed by a human operator, and also to provide a display indicative of the green and red probabilities and the nominal automatic sorting decision. The user at the workstation can review the images and the probabilities, and the automatic sorting output, and decide whether to accept or override the decision of the scanning system, if that was to allocate the item to the red or green category, or to input a decision if the scanning system decision was to allocate the item to the 'amber' category. The workstation 48 has a user input 49 that enables the user to send a signal to the sorting device 40 which can be identified by the sorting device as over-riding the decision of the scanning system. If the over-riding signal is received by the sorting device, then the sorting device does over-ride the decision of the scanning system. If no over-ride signal is received, or indeed if a confirming signal is received from the workstation confirming the decision of the scanning system, then the sorting device sorts the item on the basis of the decision of the scanning system. If the sorting system receives an 'amber' signal from the scanning system relating to an item, then it initially allocates that item to the 'red' category to be put into the red channel. However, if it receives an input signal from the workstation before it sorts the item indicating that it should be in the 'green' category, then it sorts the item to the green channel.

In a modification to the system of FIG. 6, the sorting can be fully automatic, with the processing system giving one of just two sorting outputs, 'clear' and 'not clear', allocating the item to either the green or the red channel. It would also be possible for the processing system to determine just one probability Pr(threat) with one threshold value and allocate the item to one of the two categories depending on whether the probability is above or below the threshold. In this case the allocation would still be provisional and the operator would still have the option of overriding the automatic sorting. In a further modification the automatic category allocation of the scanning system is used as the final allocation, with no user input at all. This provides a fully automated sorting system.

In the system of FIG. 6, the scan speed is matched to the conveyor velocity, so that the baggage can be moved at a constant velocity from a loading area where it is loaded onto the conveyor 20, through the scanning system 6, and on to the sorting device 40. The conveyor 20 extends for a distance L, between the exit of the scanning system 6 and the sorting device 40. During the time that a baggage item takes to travel the distance L on the conveyor 20, an operator can view the image data of the item under inspection, and the initial category allocation determined by the scanning system, and confirm or reject the automated decision of the RTT system. Typically the baggage would then be either accepted into the Clear channel and passed forward ready for transportation or rejected into the Not Cleared channel for further investigation.

In this RTT multi-focus system, the RTT scanning unit 8 is able to operate at full baggage belt speed, and hence no baggage queuing or other divert mechanism is required for optimal system operation. In integrated systems such as this, the limited throughput capability of conventional rotating source systems is a significant constraint. Often this means placing multiple conventional CT machines in parallel, and using sophisticated baggage handling systems to switch the item for inspection to the next available machine. This complexity can be avoided with the arrangement of FIG. 6.

Figure 7:
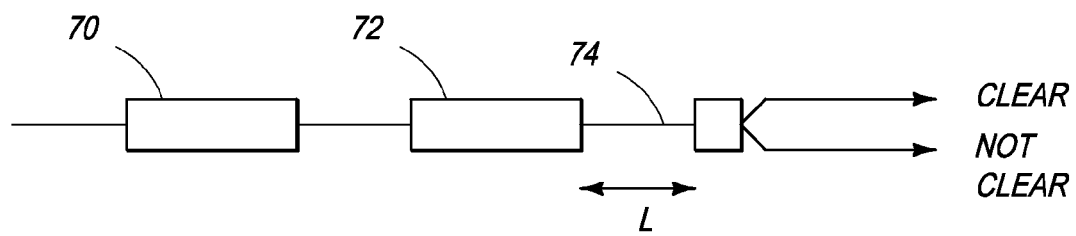
FIG. 7 is a schematic diagram of a baggage sorting system according to a further embodiment of the invention.

Referring to FIG. 7 a second embodiment of the invention comprises a redundant system in which two RTT scanning systems 70, 72 are located in series on the same conveyor 74 such that if one system were to be taken out of service, then the other could continue to scan baggage. In either case, the conveyor belt 74 would continue to run through both scanning systems 70, 72 at standard operating belt speed.

Figure 8A:
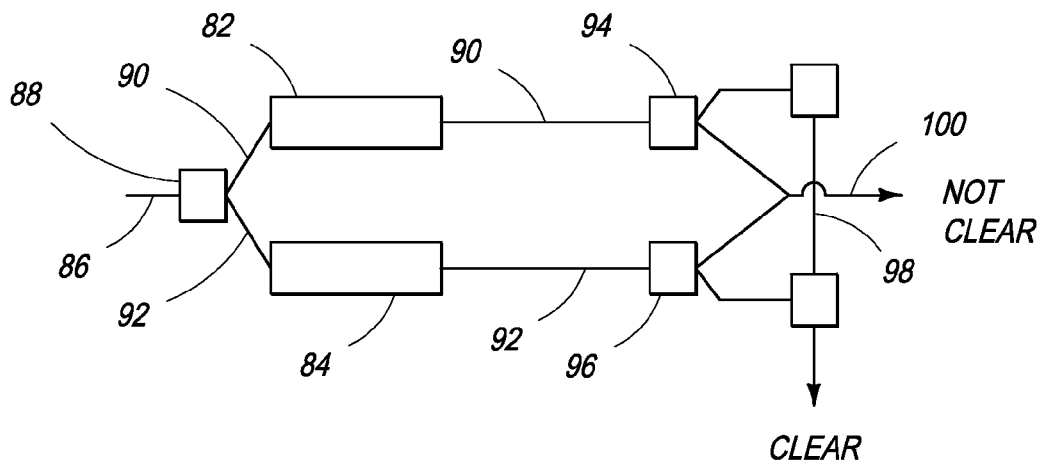
FIG. 8a is a schematic diagram of baggage sorting systems according to further embodiments of the invention.

Referring to FIG. 8a in a third embodiment there is provided a more complex redundant system in which two RTT systems 82, 84 are operated in parallel. A first main incoming conveyor 86 brings all items to be sorted to a first sorting device 88 which can transfer items onto either one of two further conveyors 90, 92. Each of these two conveyors 90, 92 passes through a respective one of the scanning systems 82, 84, which will scan the items and enable a decision to be made as to whether to clear the item or not. A further sorting device 94, 96 is provided on each of the two conveyors 90, 92 which is arranged to sort the baggage onto a common 'green channel' conveyor 98 for onward transportation, or a 'red channel' conveyor 100 if it is not cleared, where it can undergo further investigation. In this configuration, it is possible to run the input conveyor 86, and the 'green channel' conveyor at a higher speed than the RTT conveyor speed, typically up to twice the speed. For example in this case the main incoming conveyor 86 and the common 'green channel' conveyor move at a speed of 1 m/s whereas the scanning conveyors 82, 84 travel at half that speed, i.e. 0.5 m/s. Of course the system can be expanded with more parallel RTT systems, with the ratio of the speed of the main incoming conveyor to that of the scanner conveyors being equal to, or substantially equal to, the number of parallel scanners, although the sorting devices may become unreliable at more than about 1 m/s main conveyor speed.

Figure 8B:
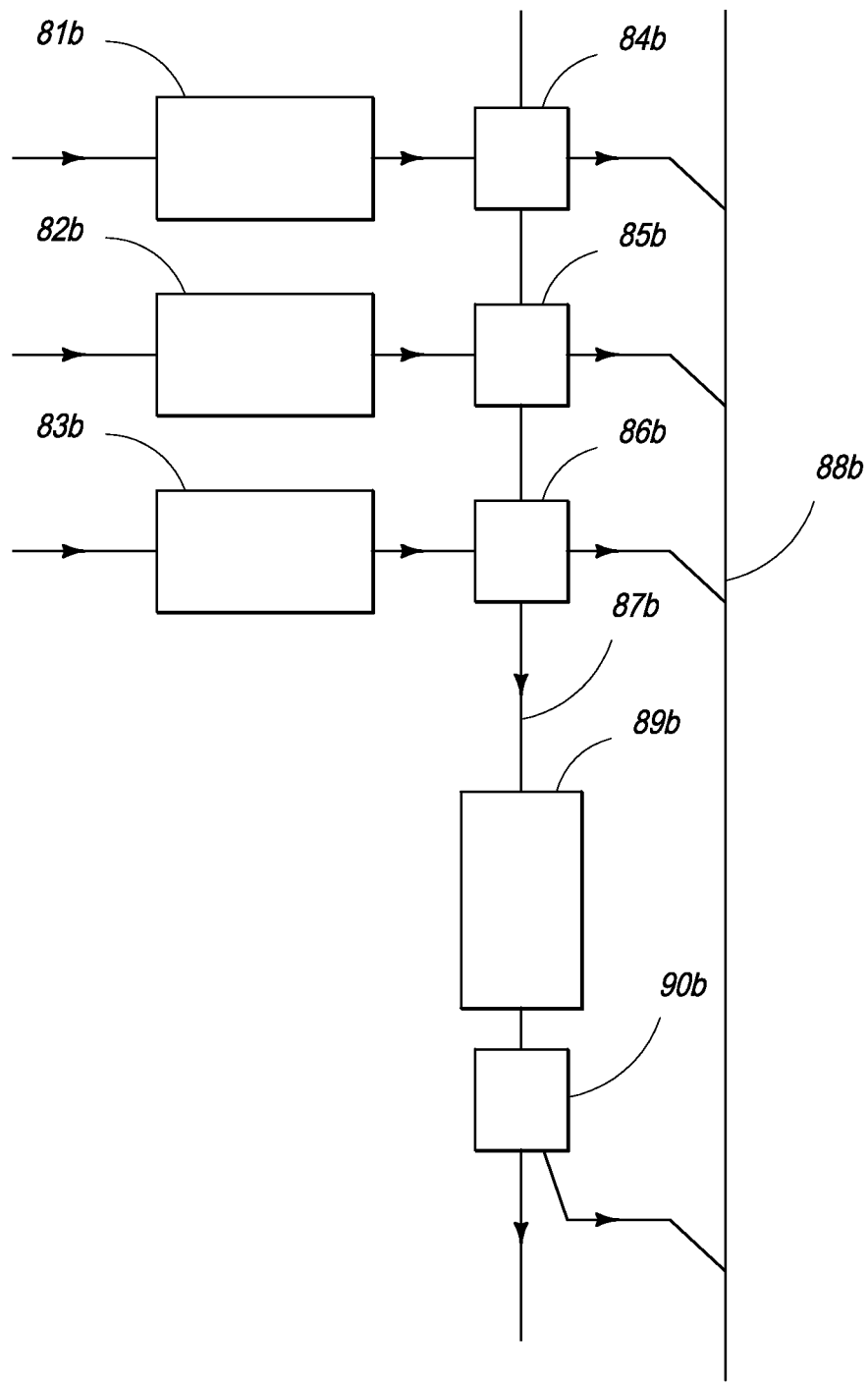
FIG. 8b is another schematic diagram of baggage sorting systems according to further embodiments of the invention.

Referring to FIG. 8b, in a further embodiment a baggage sorting system comprises a number of RTT scanners 81b, 82b, 83b, typically up to about 60 in one system, each associated with a respective check-in desk. A sorting device 84b, 85b, 86b is associated with each RTT scanner, and baggage is conveyed on a conveyor from each RTT scanner to its associated sorting device. Each sorting device 84b, 85b, 86b sorts the baggage, in response to signals from its scanner, onto either a common clear channel conveyor 88b, or a common reject channel conveyor 87b. A further backup RTT scanner 89b is provided on the reject channel conveyor 87b, with an associated sorting device 90b, that can leave baggage on the reject channel conveyor 87b, or transfer it to the clear channel conveyor 88b.

Under normal operation, each of the primary scanners 81b, 82b, 83b sorts the baggage, and the backup or redundant scanner 89b simply provides a further check on items sorted into the reject channel. If that scanner determines that an item of baggage represents no, or a sufficiently low threat, then it transfers it to the clear channel. If one of the primary scanners is not functioning or has a fault, then its associated sorting device is arranged to sort all baggage from that scanner to the reject channel. Then, the back-up scanner 89b scans all of that baggage and controls sorting of it between the clear and reject channels. This enables all the check-in desks to continue to function while the faulty scanner is repaired or replaced.

Figure 8C:
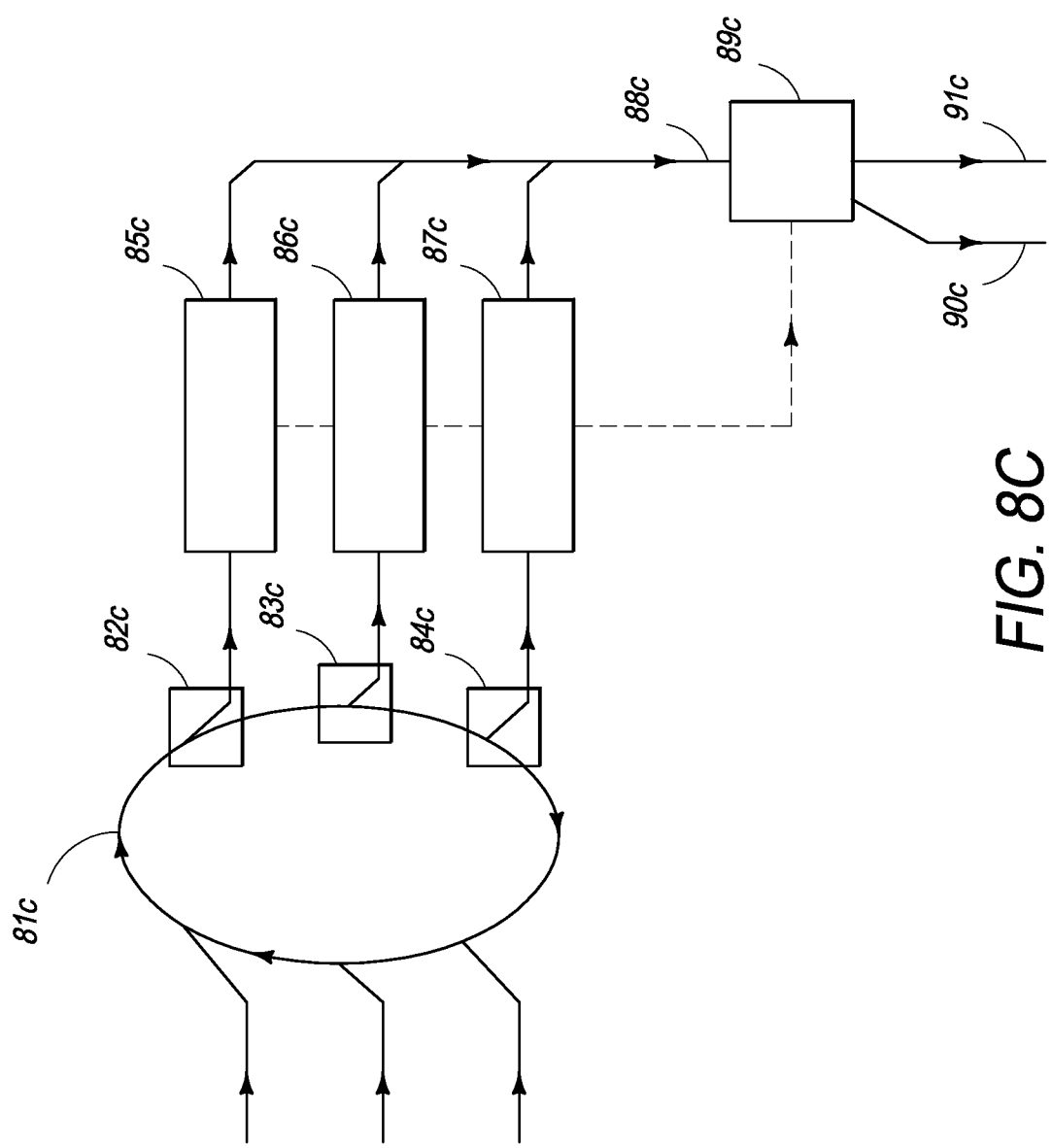
FIG. 8c is another schematic diagram of baggage sorting systems according to further embodiments of the invention.

Referring to FIG. 8c, in a further embodiment, baggage from each of the check-in desks is transferred via a plurality of separate conveyors onto a central loop or carousel 81c, on which it circulates continuously. A number of sorting devices 82c, 83c, 84c are each arranged to transfer items of baggage from the loop 81c to a respective conveyor leading to a respective RTT scanner 85c, 86c, 87c. The sorting devices 82c, 83c, 84c are controlled by the scanners to control the rate at which baggage items are fed to each of the scanners. From the scanners, conveyors transfer all of the baggage items to a common exit conveyor 88c leading to a further sorting device 89c. This is controlled by all of the scanners to sort each of the baggage items between a clear channel 90c and a reject channel 91c.

In order to track the movement of each item of baggage, each item is given a 6-digit ID, and its position on the conveyor recorded when it first enters the system. The scanners can therefore identify which item of baggage is being scanned at any one time, and associate the scanning results with the appropriate item. The sorting devices can therefore also identify the individual baggage items and sort them based on their scanning results.

The number of scanners and the speeds of the conveyors in this system are arranged such that, if one of the scanners is not functioning, the remaining scanners can process all of the baggage that is being fed onto the loop 81c from the check-in desks.

In a modification to this embodiment, the sorting devices 82c, 83c, 84c that select which items are transferred to each scanner are not controlled by the scanners, but are each arranged to select items from the loop 81c so as to feed them to the respective scanner at a predetermined rate.

Figure 9:
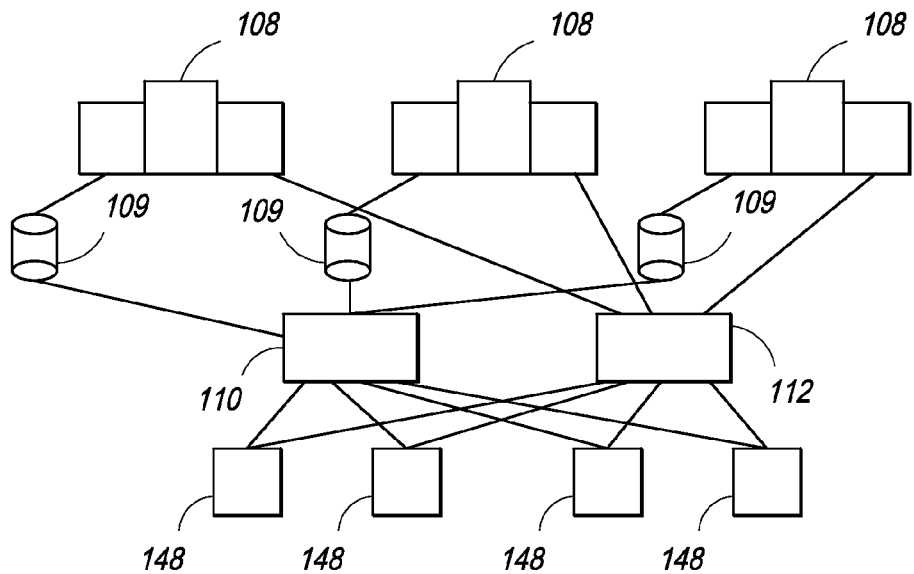
FIG. 9 is a schematic diagram of a networked baggage sorting system according to a further embodiment of the invention.

Referring to FIG. 9 a networked system according to a further embodiment comprises three scanning systems 108 similar to that of FIG. 6, and four operator workstations 148. The video image outputs from the three RTT scanning systems 108 are connected via respective high bandwidth point-to-point video links to real time disk arrays 109 which providing transient storage for the raw image data, to a redundant video switch 110. The disk arrays 109 are in turn connected to each of the workstations 148. The video switch 110 is therefore able to transmit the raw video image output from each of the scanning systems 108 from its temporary storage, to any one of the workstations 148, where it can be used to create 3-dimensional video images which can be viewed off-line. The outputs from the scanning system for the red/green probability signals and the automatic sorting allocation signals are connected to a redundant conventional Ethernet switch 112, which is also connected to each of the workstations. The Ethernet switch is arranged to switch each of the probability signals and the sorting allocation signals to the same workstation 148 as the associated video signal. This allows image data from the multiple machines together with the automatic allocation and probabilities assigned to the allocation, to be switched through to the bank of operator workstations 148 where an operator can both monitor the performance of the baggage inspection system and determine the destination of baggage assigned an amber threat level.

Alternatively, a networked system comprises a single scanning system 108 connected to a server and a workstation 148. The video image output from the scanning system 108 is connected to a real time disk array 109, which provides transient storage for the raw image data. The disk array 109 is in turn connected to the workstation 148. The probability signal and allocation signal outputs are sent to the workstation 148 together with the associated video image output to be monitored by an operator. The networked single scanning system may be part of a networked system with multiple scanning systems.

Figure 10:
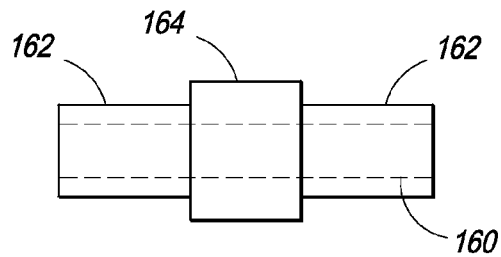
FIG. 10 is a schematic plan view of a stand-alone scanning system according to a further embodiment of the invention.
Figure 11:
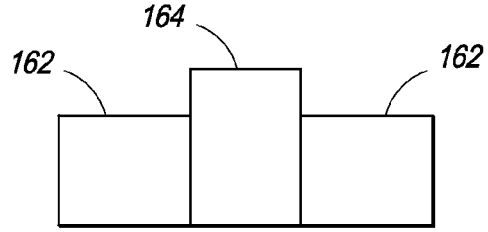
FIG. 11 is a schematic side view of the system of FIG. 10.

Referring to FIGS. 10 and 11, in a further embodiment an in-line scanner has a conveyor belt 160 just as long as the main scatter shields 162. In such standalone system configurations, the item for inspection is placed onto the conveyor belt 160 and the item loaded into the system. The item is then scanned through the scanner machine 164 and images are generated. Often, in conventional systems, the item is pre-screened with a simple transmission X-ray system to identify likely threat areas prior to computed tomography screening of selected planes in the object. Such applications are simple for a real-time multi-focus system to cope with. Here, no pre-screening would be used and a true three-dimensional image of the complete item would be obtained.

In some embodiments the locus of source points in the multi-focus X-ray source will extend in an arc over an angular range of only 180 degrees plus the fan beam angle (typically in the range 40 to 90 degrees). The number of discrete source points is advantageously selected to satisfy the Nyquist sampling theorem. In some embodiments, as in that of FIG. 1, a complete 360 degree ring of source points is used. In this case, the dwell-time per source point is increased over a 180+ fan beam configuration for a given scan rate and this is advantageous in improving reconstructed image signal-to-noise ratio.

Figure 12:
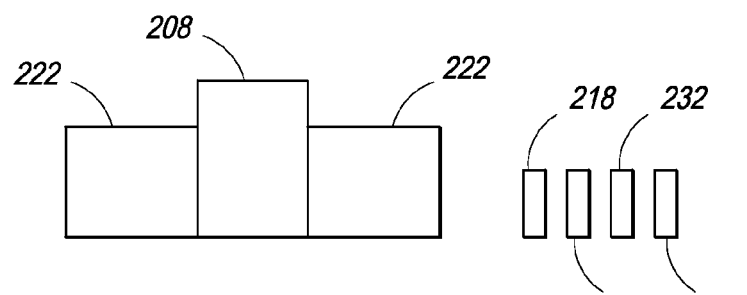
FIG. 12 is a schematic side view of a modular scanning system according to a further embodiment of the invention.

The scanner system of FIG. 1 is an integrated scanner system, in that the control, processing, power supply, and cooling units 18, 30, 32, 34 are housed in a unit with the scanning system 8 and the screening 22. Referring to FIG. 12, in a further embodiment there is provided a modular system in which some, or all, of the control, processing, power supply, and cooling racks 218, 230, 232, 234 are located remotely from the scanning unit 208 comprising multi-focus X-ray source and sensor array. It is advantageous to use a modular design to facilitate easy installation, particularly in baggage handling hall environments, where systems may be suspended from the ceiling or in regions with restricted access. Alternatively, a complete system can be configured as an integrated unit with the sub-assembly units co-located within a single housing.

In some embodiments, including that of FIG. 1, a single X-ray detector ring is used. This is inexpensive to construct and provides adequate signal-to-noise performance even at high image scanning rates with a simple fan-beam image reconstruction algorithm. In other embodiments (particularly for large image reconstruction circle diameter) it is preferable to use a multi-ring sensor array with a plurality of circular or part-circular groups of sensors arranged adjacent to each other, spaced along the axis of the system offset from the source. This enables a more complex cone-beam image reconstruction algorithm to be used in the processing system.

The use of a multi-ring sensor increases dwell-time per source point resulting in larger integrated signal size and consequent improvement in signal-to-noise ratio in the reconstructed image.

Central to the design of the embodiments described above, which use a multi-focus X-ray source based computed tomography system, is the relationship between the angular rotational speed of the source and the velocity of the conveyor system passing through the scanner. In the limit that the conveyor is stationary, the thickness of the reconstructed image slice is determined entirely by the size of the X-ray focus and the area of the individual elements of the X-ray detector array. As conveyor speed increases from zero, the object under inspection will pass through the imaging slice during rotation of the X-ray beam and an additional blurring will be introduced into the reconstructed image in the direction of the slice thickness. Ideally, the X-ray source rotation will be fast compared to the conveyor velocity such that blurring in the slice thickness direction will be minimized.

A multi-focus X-ray source based computed tomography system for baggage inspection provides a good ratio of angular source rotational speed to linear conveyor speed for the purposes of high probability detection of threat materials and objects in the item under inspection. As an example, in the embodiment of FIG. 1, the conveyor speed is 0.5 m/s as is common in airport systems. The source can achieve 240 source rotations about the conveyor per second, so the object under inspection will move a distance of 2.08 mm through the imaging slice during the scan. In a conventional system with source rotation of 4 revolutions per second, the object under inspection will move a distance of 62.5 mm through the imaging slice during the scan at the same belt speed.

The primary goal of an inspection system for detection of threat materials is to detect accurately the presence of threat materials and to pass as not suspect all other materials. The larger the blurring in the slice direction that is caused by conveyor motion during a scan, the greater the partial volume artifact in the reconstructed image pixel and the less accurate the reconstructed image density. The poorer the accuracy in the reconstructed image density, the more susceptible the system is to provide an alarm on non-threat materials and to not raise an alarm on true threat materials. Therefore, a real-time tomography (RTT) system based on multi-focus X-ray source technology can provide considerably enhanced threat detection capability at fast conveyor speeds than conventional mechanically rotated X-ray systems.

Due to the use of an extended arcuate anode in a multi-focus X-ray source, it is possible to switch the electron source such that it jumps about the full length of the anode rather than scanning sequentially to emulate the mechanical rotation observed in conventional computed tomography systems. Advantageously, the X-ray focus will be switched to maximize the distance of the current anode irradiation position from all previous irradiation positions in order to minimize the instantaneous thermal load on the anode. Such instantaneous spreading of the X-ray emission point is advantageous in minimizing partial volume effect due to conveyor movement so further improving reconstructed pixel accuracy.

The high temporal resolution of RTT systems allows a high level of accuracy to be achieved in automated threat detection. With this high level of accuracy, RTT systems can be operated in unattended mode, producing a simple two-state output indication, with one state corresponding to a green or clear allocation and the other to a red or not clear allocation. Green bags are cleared for onward transport. Red bags represent a high level of threat and should be reconciled with the passenger and the passenger barred from traveling.

Further embodiments of the invention will now be described in which data relating to the scattering of X-rays as well as that relating to transmitted X-rays is recorded and used to analyze the scanned baggage items.

Figure 13:
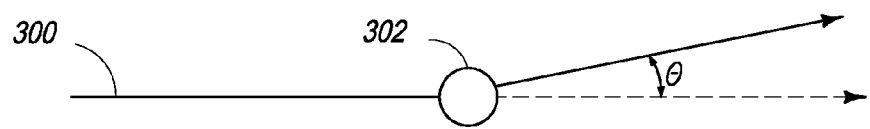
FIG. 13 is a diagram of an X-ray scattering event.

Referring to FIG. 13 when a beam 300 of X-rays passes through an object 302, some of the X-rays are transmitted straight through it, and exit the object traveling in the same direction as they entered it. Some of the X-rays are scattered through a scattering angle θ, which is the difference between the direction in which they enter the object and the direction in which they leave it. As is well known there are two types of scattering that occur: coherent or Bragg scattering, which is concentrated around scattering angles of 5 degrees, typically in the range 4 degrees to 6 degrees, and incoherent or Compton scattering in which the X-ray is scattered through larger angles. Bragg scattering increases linearly with the atomic number of the object and obeys the formula:

$$n\lambda = 2d \sin \theta$$

where n is an integer, λ is the wavelength of the X-ray, and d is the inter-atomic distance in the object.

Therefore the amount of Bragg scattering gives information about the atomic structure of the object. However, it does not vary smoothly with atomic number.

The amount of Compton scattering is dependent on, and varies smoothly with, the electron density of the object, and therefore the amount of scattering at higher scatter angles gives information about the electron density of the object, and hence about its atomic number.

Figure 14:
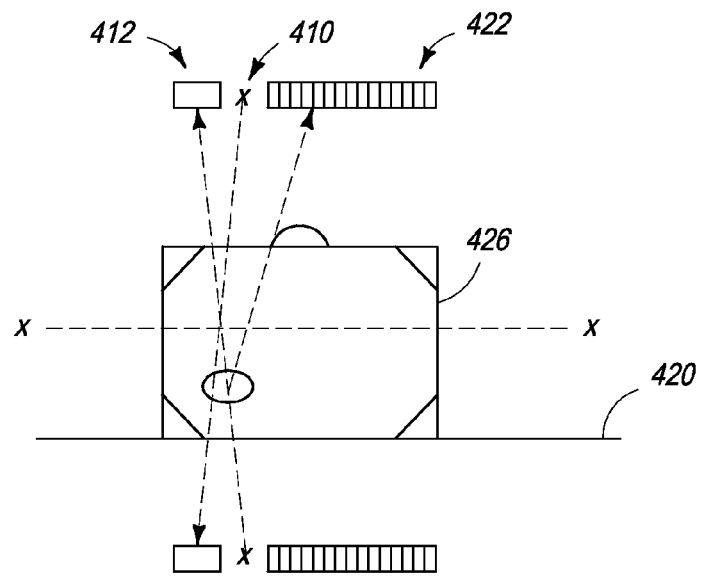
FIG. 14 is a longitudinal section through a security scanning system according to a further embodiment of the invention.

Referring to FIG. 14 a security scanning system according to a further embodiment of the invention comprises a multi-focus X-ray source 410 which is the same as that of FIG. 1, and a circular detector array 412 and conveyor 420 that are also the same as those of FIG. 1. However, in this embodiment, the system comprises a further cylindrical array of detectors 422 which also extends around the conveyor at the same radius as the circular detector array 412 but on the other side axially of the source 410. Whereas the circular detector array is arranged to detect X-rays transmitted through the object 426, the cylindrical detector array 422 is arranged to detect X-rays scattered in the object. The scatter detector array 422 is made up of a number of circular arrays or rings 422a, 422b of detectors, and the detectors in each ring are equally spaced around the conveyor so that they are arranged in a number of straight rows extending in the axial direction of the scanner.

The detectors in the scatter detector array 422 are energy resolving detectors such that individual X-ray interactions with each detector produce a detector output that is indicative of the energy of the X-ray. Such detectors can be fabricated from wide bandgap III-V or II-IV semiconductor materials such as GaAs, HgI, CdZnTe or CdTe, a narrow gap semiconductor such as Ge, or a composite scintillation detector such as NaI(Ti) with photomultiplier tube readout.

Figure 15:
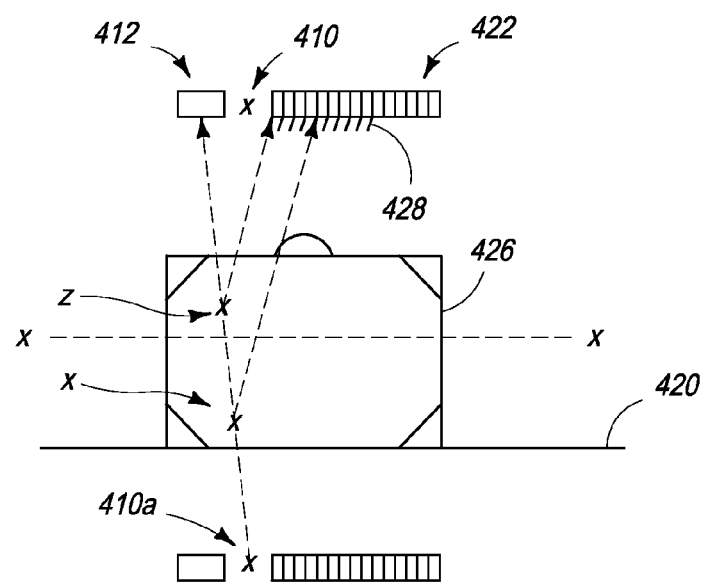
FIG. 15 is a further longitudinal section through the system of FIG. 14 showing how different scatter events are detected.
Figure 16:
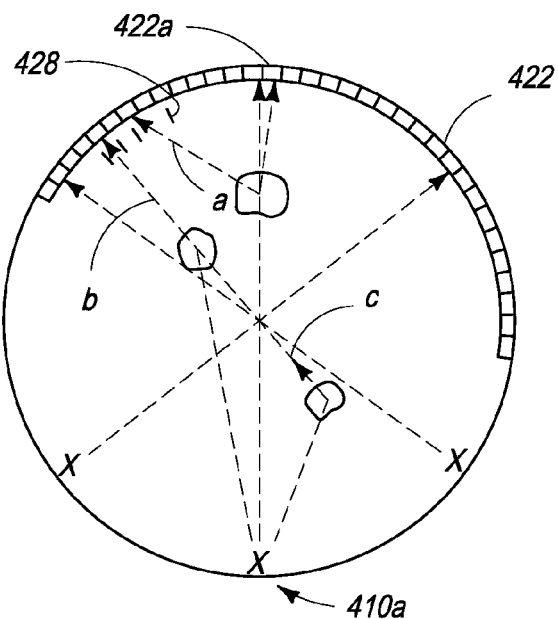
FIG. 16 is a transverse section through the system of FIG. 14.

Referring to FIG. 15, a collimator 428 is provided in front of the scattering detectors 422. The collimator 428 provides a barrier that prevents X-rays from reaching each detector unless it comes from a particular receiving direction. For each detector in the array 422, the receiving direction passes through the central longitudinal axis X-X of the scanner, as can be seen in FIG. 16. However, the receiving direction is not perpendicular to the axis X-X, but is inclined at about 5.degree. to the plane of the detector rings 422a, 422b in the direction towards the source 410, as can be seen in FIG. 15.

Referring to FIG. 15 it will be appreciated that X-rays incident on any one of the detectors of the array 422 must have been scattered from a respective small sub-volume within the thin imaged volume that lies both in the path of the X-ray beam and in the line of the receiving direction from the detector 422. For any coherently scattered X-rays, the axial position of the detector that detects it will be determined by the distance from the active X-ray source point at which the scattering occurred. Detectors nearest the source 410 in the axial direction will detect X-rays scattered furthest from the active X-ray source point. For example X-rays scattered from the point x, which is nearest the active X-ray source point 410a, will be detected by a detector further from the source 410 than X-rays scattered from the point z which is further from the active X-ray source point. Therefore, at any one time, when the active X-ray source point can be identified, the axial position of the detector which detects the scattered X-ray can be used to determine the position of the scattering along the X-ray beam direction.

It will also be appreciated from FIG. 15 that, for this system to work, it is important that the X-ray beam should be narrowly focused in the axial direction of the scanner. Spreading of the beam in the transverse direction, e.g. use of a fan beam spread in the transverse direction will still allow this positioning of coherent scattering events.

Referring to FIG. 16, because the collimator 428 is directed towards the axis of the scanner, X-rays from an active source point 410a that undergo coherent scattering will only be detected by the row of detectors 422a that is on the opposite side of the scanner axis to the active source point, and possibly one or more of the rows close to it on either side depending on how narrowly focused the collimator is. If X-rays are confined to a straight narrow 'pencil' beam, then any X-rays that are scattered incoherently through larger angles will not be detected at all as they will be cut off by the collimator 428. An example of such an X-ray is shown by arrow 'a' in FIG. 16. However, if a fan beam of X-rays is produced from the active source point 410a, that is spread out through the imaging volume slice in the direction perpendicular to the scanner axis, then X-rays directed further away from the scanner axis can undergo incoherent scattering and reach detectors to either side of the row 422a opposite the active source point. Examples of such X-rays are shown by the arrows b and c. It will be noted that, to reach any detector 422b, the scattering event must take place in the plane passing through the scanner axis and that detector 422b. This means that, for a given active source point and a particular detector, the position of the scattering event of a detected X-ray can be identified as being in the plane passing through the scanner axis and that detector. If the exact position of the scattering event is to be determined then other information is needed. For example if information regarding the position of objects within the imaging volume is available, for example from tomographic imaging data, then the scattering can be associated with the most likely object as will be described in more detail below.

From the Bragg scattering data, for each detected scattering event, the combination of the X-ray energy and the scatter angle can be used to determine the inter-atomic distance d of the material in which the scattering event took place. In practice, the scatter angle can be assumed to be constant, and the energy used to distinguish between different materials. For the Compton scattering, the level of scattering from each volume of the scanning volume gives an indication of the density of the material in that volume. The ratio of Compton to coherent scatter can also be determined and used as a further parameter to characterize the material of the imaged object.

Due to the short dwell time for each X-ray source point, the number of detected scattered X-rays for each source point will always be very low, typically less than five. In order to form a reasonable coherent scatter signal it is necessary to collect scatter data for all source points within a tomographic scan and then accumulate the results for each sub-volume of the imaging volume. For a scanner with 500 source points, and an average of one coherent diffraction scatter result per sub-volume per scan, then following accumulation of the set of data, each sub-volume will have 500 results associated with it, corresponding to 500 scattering events within that sub-volume. A typical sub-volume occupies an area within the imaging plane of a few square centimeters, with a volume thickness of a few millimeters.

Figure 17:
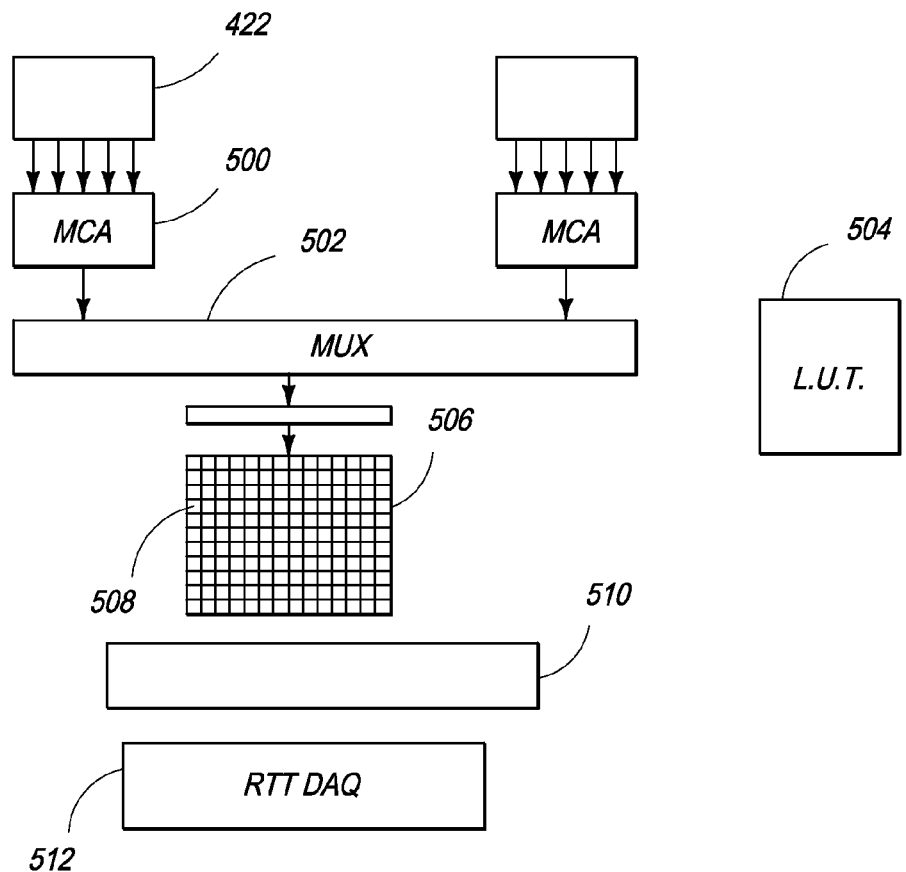
FIG. 17 is a schematic diagram of a data acquisition system of the scanning system of FIG. 14.

Referring to FIG. 17, the data acquisition system arranged to accumulate data from the scatter detector array 422 of the scanner of FIGS. 14 to 16 comprises a multi-channel analyzer 500 associated with each of the detectors 422. Each MCA 500 is arranged to receive the output signals from the detector, and allocate each X-ray detected to one of a number of X-ray energy ranges or channels, and output a signal indicative of the energy range in which the detected X-ray falls. A multiplexer 502 is arranged to receive the outputs from each of the MCAs 500. A look-up table 504 is also provided which has entries in it that, for a given source point and detector, identify the sub-volume within the imaging volume in which the X-ray was scattered. The system further comprises an image memory 506 which includes a number of memory areas 508, each of which is associated with a respective sub-volume within the scanner imaging plane.

Data is loaded into each memory area 508 automatically by the multiplexer 502 under the direction of the look up table 504. The look up table is loaded with coefficients prior to scanning that map each combination of detector 422 and MCA 500 to a respective image location 508, one look up table entry per X-ray source position. Those pixels, i.e. detectors 422, that are in the forward direction, i.e. substantially in the direction that the photon is traveling from the source prior to any interaction, are assumed to record coherent scatter photons at small beam angles of about 4-6 degrees. Those pixels 422 that are not in the forward direction are assumed to record incoherent scattered photons due to the Compton scattering effect. Hence, the image memory 506 is actually "three dimensional"—two dimensions represent location in the image while the third dimension holds scattered energy spectra for both coherent (lo 8-bits) and incoherent scattering (hi 8 bits). The look up table 504 will also instruct the multiplexer 502 as to the type of data that is being collected for each MCA 500 at each projection so that the appropriate memory space is filled.

Once the scatter data has been collected for a given scan, the data is transferred to and synchronized, by a projection sequencer 510, with the main RTT data acquisition system 512, which is described above with reference to FIG. 4. Hence the reconstructed image data and scatter data are passed through simultaneously to the threat detection system, which can use it to determine suitable parameters for analysis.

For each scan, the tomographic image data from the transmission detectors 412 produces data relating to the X-ray attenuation for each pixel of the image, which in turn corresponds to a respective sub-volume of the tomographic imaging volume. This is obtained as described above with reference to FIG. 4. The data from the scatter detectors 422 provides, as described above, data relating to the amount of coherent scattering within each sub-volume, and data relating to the amount of incoherent scattering within each sub-volume. This data can therefore be analyzed in a threat detection processor similar to that of FIG. 5. In this case the parameters of the data which are extracted can relate to the image data or the scatter data or combinations of two or more types of data.

Examples of parameters that are extracted from the data are the ratio of coherent to incoherent scatter, material types as determined from coherent scatter data, material density as determined from incoherent scatter data, correlation of CT image pixel values with scatter data. Also parameters for the scatter data corresponding to those described above for the transmission data can also be determined.

Figures 18, 19:
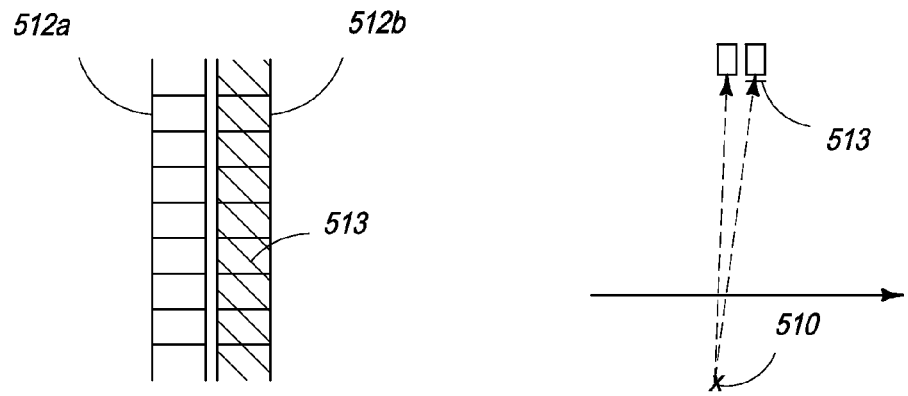
FIG. 18 is a partial view of a dual energy scanner according to a further embodiment of the invention.
FIG. 19 is a further partial view of the scanner of FIG. 18.

Referring to FIG. 18, in a further embodiment of the invention the transmission detectors 512 that are used to generate the tomographic image data are arranged to measure the X-ray transmission over different energy ranges. This is achieved by having two sets of detectors 512a, 512b, each forming a ring around the conveyor. The two sets are at different axial locations along the direction of travel of the conveyor, in this case being adjacent to each other in the axial direction. The first set 512a has no filter in front of it, but the second set 512b has a metal filter 513 placed between it and the X-ray source 510. The first set of detectors 512a therefore detects transmitted X-rays over a broad energy range, and the second set 512b detects X-rays only in a narrower part of that range at the high energy end.

As the item to be scanned moves along the conveyor, each thin volume or slice of it can be scanned once using the first set of detectors 512a and then scanned again using the second set 512b. In the embodiment shown, the same source 510 is used to scan two adjacent volumes simultaneously, with data for each of them being collected by a respective one of the detector sets 512a, 512b. After a volume of the item has moved past both sets of detectors and scanned twice, two sets of image data can be formed using the two different X-ray energy ranges, each image including transmission (and hence attenuation) data for each pixel of the image. The two sets of image data can be combined by subtracting that for the second detector set 512a from that of the first 512b, resulting in corresponding image data for the low energy X-ray component.

The X-ray transmission data for each individual energy range, and the difference between the data for two different ranges, such as the high energy and low energy, can be recorded for each pixel of the image. The data can then be used to improve the accuracy of the CT images. It can also be used as a further parameter in the threat detection algorithm.

It will be appreciated that other methods can be used to obtain transmission data for different ranges of X-ray energies. In a modification to the system of FIGS. 18 and 19, balanced filters can be used on the two detector sets. The filters are selected such that there is a narrow window of energies that is passed by both of them. The image data for the two sets of detectors can then be combined to obtain transmission data for the narrow energy window. This enables chemical specific imaging to be obtained. For example it is possible to create bone specific images by using filters balanced around the calcium K-edge energy. Clearly this chemical specific data can be used effectively in a threat detection algorithm.

In a further embodiment, rather than using separate filters, two sets of detectors are used that are sensitive to different energy X-rays. In this case stacked detectors are used, comprising a thin front detector that is sensitive to low energy X-rays but allows higher energy X-rays to pass through it, and a thick back detector sensitive to the high energy X-rays that pass through the front detector. Again the attenuation data for the different energy ranges can be used to provide energy specific image data.

In a further embodiment two scans are taken of each slice of the object with two different X-ray beam energies, achieved by using different tube voltages in the X-ray source, for example 160 kV and 100 kV. The different energies result in X-ray energy spectra that are shifted relative to each other. As the spectra are relatively flat over part of the energy range, the spectra will be similar over much of the range. However, part of the spectrum will change significantly. Therefore comparing images for the two tube voltages can be used to identify parts of the object where the attenuation changes significantly between the two images. This therefore identifies areas of the image that have high attenuation in the narrow part of the spectrum that changes between the images. This is therefore an alternative way of obtaining energy specific attenuation data for each of the sub-volumes within the scanned volume.

Figures 20, 21, 22:
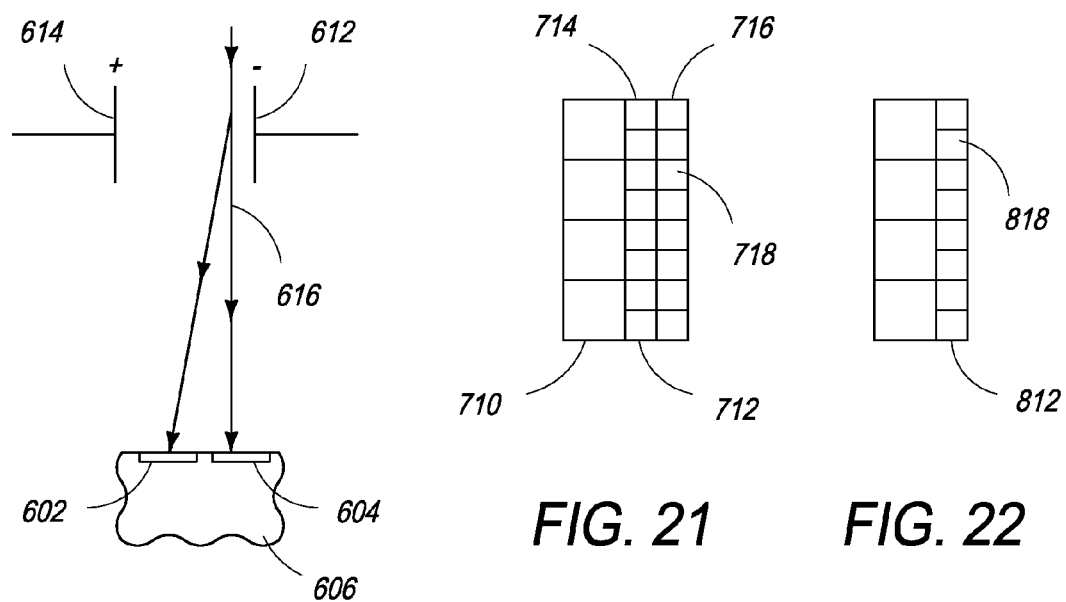
FIG. 20 is a schematic view of a dual energy X-ray source of a further embodiment of the invention.
FIG. 21 is a schematic view of a detector array of a scanner according to a further embodiment of the invention.
FIG. 22 is a schematic view of a detector array of a scanner according to a further embodiment of the invention.

Referring to FIG. 20 in a further embodiment of the invention, two different X-ray energy spectra are produced by providing an anode 600 in the X-ray tube that has target areas 602, 604 of two different materials. In this case, for example, the anode comprises a copper base 606 with one target area 602 of tungsten and one 604 of uranium. The electron source 610 has a number of source points 612 that can be activated individually. A pair of electrodes 612, 614 is provided on opposite sides of the path of the electron beam 616 which can be controlled to switch an electric field on and off to control the path of the electron beam so that it strikes either one or the other of the target areas 602, 604. The energy spectrum of the X-rays produced at the anode will vary depending on which of the target areas is struck by the electron beam 616.

This embodiment uses an X-ray source similar to that of FIG. 1a, with the different target areas formed as parallel strips extending along the anode 27. For each active electron source point two different X-ray spectra can be produced depending on which target material is used. The source can be arranged to switch between the two target areas for each electron source point while it is active. Alternatively the scan along the anode 27 can be performed twice, once for one target material and once for the other. In either case further electron beam focusing wires may be needed to ensure that only one or the other of the target materials is irradiated by the electron beam at one time.

Depending on the angle at which the X-ray beam is extracted from the anode, the beams from the two target areas 602, 604 can in some cases be arranged to pass though the same imaging volume and be detected by a common detector array. Alternatively they may be arranged to pass through adjacent slices of the imaging volume and detected by separate detector arrays. In this case the parts of the imaged item can be scanned twice as the item passes along the conveyor in a similar manner to the arrangement of FIG. 18.

Referring to FIG. 21, in a further embodiment, two detector arrays are provided in a single scanner, adjacent to each other in the axial direction, one 710 corresponding to that of FIG. 1 and being arranged to form a RTT image, and the other, 712, being of a higher resolution, and being arranged to produce a high resolution projection image of the scanned object. In this embodiment the high resolution detector array 712 comprises two parallel linear arrays 714, 716 each arranged to detect X-rays at a different energy, so that a dual energy projection image can be produced. In the embodiment of FIG. 22, the high resolution array 812 comprises two stacked arrays, a thin array on top arranged to detect lower energy X-rays but transparent to higher energy X-rays, and a thicker array beneath arranged to detect higher energy X-rays. In both cases, the two detector arrays are arranged close enough together in the axial direction to be able to detect X-rays from a single linear array of source points.

Figure 23:
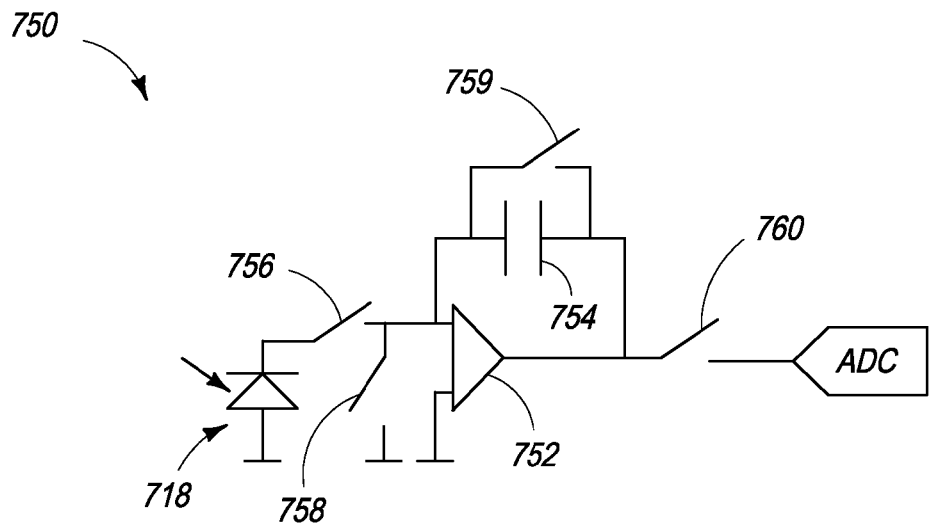
FIG. 23 is a circuit diagram of a data acquisition circuit of the embodiment of FIG. 21.

In order to provide a projection image, data needs to be captured from all of the detectors in the high resolution array 712, 812 when only one source point is active. Referring to FIG. 23, in order to do this each detector 718, 818 in the high resolution array is connected to an integrator 750. The integrator comprises an amplifier 752 in parallel with a capacitor 754. An input switch 756 is provided between the detector 718 and the amplifier 752, a reset switch 758 is provided across the input terminals of the amplifier, and a further reset switch 759 connected across the capacitor 754, and a multiplexing switch 760 is provided between the integrator and an analogue to digital converter ADC.

In operation, while the detector 718 is not required to be active, all of the switches except for the multiplexing switch 760 are closed. This ensures that the capacitor 754 is uncharged and remains so. Then, at the start of the period when the detector is required to gather data, the two reset switches 758, 759 are closed so that any X-rays detected by the detector 718 will cause an increase in the charge on the capacitor 754, which results in integration of the signal from the detector 718. When the period for data collection has ended, the input switch 756 is opened, so that the capacitor will remain charged. Then, in order for the integrated signal to be read from the integrator, the output switch 760 is closed to connect the integrator to the ADC. This provides an analogue signal to the ADC determined by the level of charge on the capacitor 754, and therefore indicative of the number of X-rays that have been detected by the detector 718 during the period for which it was connected to the integrator. The ADC then converts this analogue signal to a digital signal for input to the data acquisition system. To produce a single projection image, all of the high resolution detectors are used to collect data at the same time, when one of the X-ray source points is active.

Figure 24:
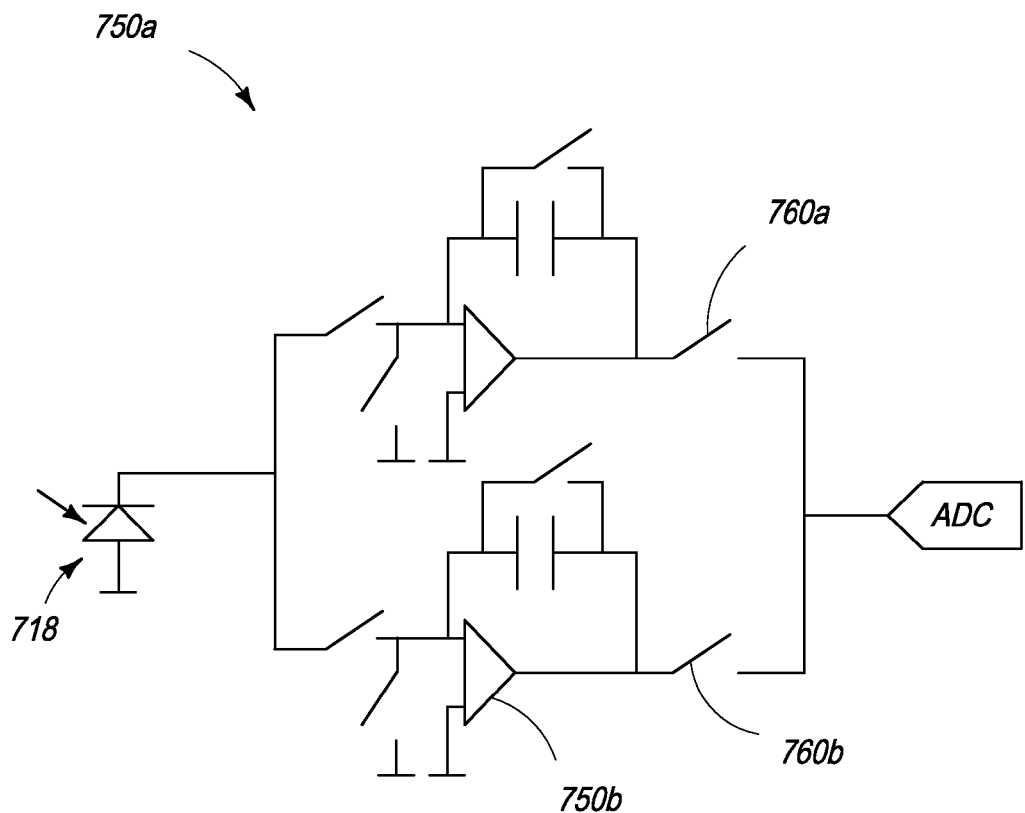
FIG. 24 is a circuit diagram of a data acquisition circuit of a further embodiment of the invention.

Referring to FIG. 24, in a further embodiment, each detector 718 is connected to two integrators 750a, 750b in parallel, each of which is identical to that of FIG. 23. The outputs from the two integrators are connected via their output switches 760a, 760b to an ADC. This enables each integrator to be arranged to integrate the signal from the detector 718 at a different point in the scan of the X-ray source, and therefore to collect data for a separate image, the two images being from different angles with different X-ray source points. For example this can be used to produce projection images from orthogonal directions which can be used to build up a high resolution 3-dimensional image, from which the position of features in the imaged package can be determined in three dimensions.

The high resolution image can be useful when combined with the RTT image, as it can help identify items for which higher resolution is needed, such as fine wires.

In another embodiment of the present invention, a high speed tomographic scanner is disclosed which is capable of screening baggage and cargo items at full conveyor speed. This is achieved by substituting the mechanically scanned gantry which is used in known security screening systems with an electronically scanned X-ray source and associated detection methods. The performance characteristics of such a system provide for automated detection of explosives and explosive devices in a single scanning pass with follow-on human image visualisation in those cases where the automated detection algorithm locates a suspect material or device.

The present invention is characterised by high image quality in combination with high scanning throughput. A scanner within the scope of the present invention can achieve a spatial resolution of the order of 2 mm or less in all three dimensions, with a reconstructed pixel size in the three-dimensional image of 1.5 mm or less in all three dimensions. Scanners can be configured to achieve such image resolution characteristics while simultaneously operating with conveyors with scanning speed of 0.25 m/s and above with a reconstructed image signal to noise ratio above 50 and generally above 100. This image quality provides sufficient information to unambiguously determine both the volume and shape of potentially explosive materials with an accuracy of measurement of the material linear attenuation coefficient of typically 1%.

Notwithstanding the high image quality, high scanning throughput and interactive three-dimensional image display capability of such a system, there are still occasions where an explosive material or explosive device is suspected and would benefit from additional screening. In particular, a suspect explosive material or device in a baggage or cargo item that has been inspected using the high speed electronically scanned X-ray source scanner of the present invention can be further investigated by a secondary method to confirm the presence, or absence, of an explosive material.

In order to improve on the inspection capability of the high speed X-ray system, a secondary sensor must probe one or more chemical properties of the material itself and the specific signal generated from the probe must then be correlated back to the shape, volume and expected type of explosive material which has been detected through the X-ray inspection process.

Additionally, the detailed X-ray image must be used to target the secondary confirmatory sensor to the specific region of the baggage or cargo item under inspection in order to maximise the performance of the secondary sensor.

Figure 25:
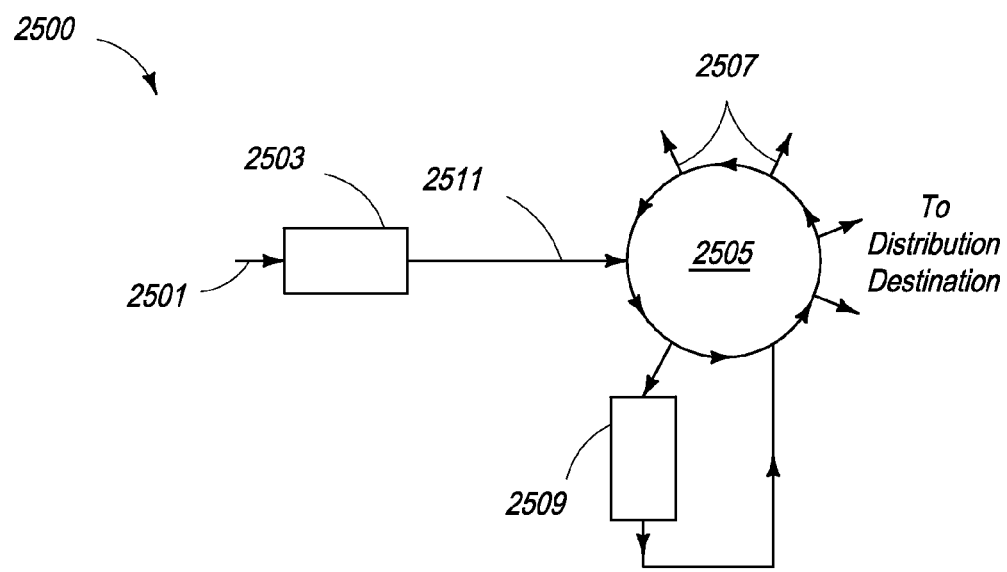
FIG. 25 is one embodiment of a baggage handling system with a diversion loop.

As shown in FIG. 25, a baggage handling system 2500 is generally required to relocate the object under inspection from the high throughput X-ray system into a secondary scanning region. Baggage and cargo items, such as checked baggage in an airport environment, enter the system 2500 from the left 2501. Baggage and cargo items are screened using a high-speed X-ray scanner 2503 comprising an electronically switched X-ray source and associated X-ray detection, image reconstruction and threat detection sub-systems, as disclosed above.

Baggage follows a conveyor system 2511 to a sorting device 2505 which is configured as a loop on which baggage and cargo items remain until they have been security cleared for onwards travel, at which point the sorting system 2505 may eject the baggage or cargo item to one of a number of destinations 2507. In an airport, each destination will preferably correspond to a direction of a specific departing flight.

Baggage and cargo items that are marked as a threat following X-ray scanning, automatic detection and human visualisation are routed by the conveyor system and sorting device 2511, 2505 to a second confirmatory sensor 2509. Advantageously in this design, the confirmatory sensor 2509 is allowed to take a considerable period of time to analyze the baggage or cargo item without impeding the flow of baggage and cargo items through to their destination.

Figure 26:
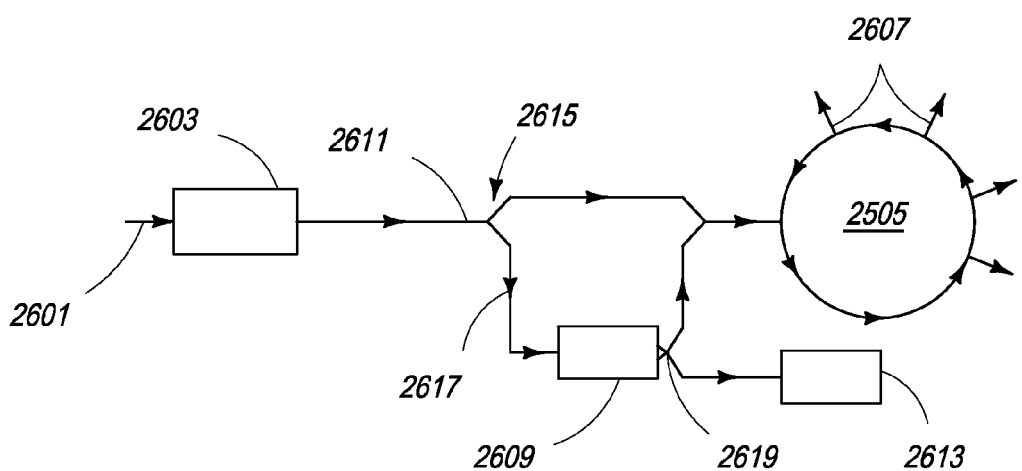
FIG. 26 is another embodiment of a baggage handling system with a diversion loop.

In some situations, it is advantageous that only cleared bags are allowed into the main sorting system. Referring to FIG. 26, a secondary loop 2617 is provided for the confirming sensor 2609. Here, baggage and cargo items, which enter from the left 2601, that have been cleared by the X-ray system 2603 proceed straight through a divert point 2615 and onwards to the main sorting loop 2605 and to their ultimate destination 2607. Baggage that has been marked as potentially having one or more threat items by the X-ray system 2603 are subsequently viewed by an operator while the baggage and cargo items continue towards the divert point 2615 on the conveyor system 2611. If the operator has not cleared a baggage or cargo item by this point 2615, the item is automatically diverted into a side loop 2617 which contains the confirmatory sensor 2609. Baggage or cargo items which still require additional manual screening can be diverted to a screening area 2613 while cleared baggage can be sent onward to the main sorting loop 2605.

In both of the aforementioned embodiments, the conveyor system is advantageously formed from multiple short conveyor sections (typically 1.5 to 2 m long) such that a plurality of items can be queued for scanning. Preferably, queuing slots for 5 to 20 baggage and cargo items shall be made available. Baggage and cargo items are passed one item at a time into the confirmatory sensor. If the human operator has completed their inspection of a baggage or cargo item while the item has been queuing and has marked the item as being clear, then the baggage or cargo item can be passed straight through the confirmatory scanner without further delay and back into the main sorting loop, 2505, 2605. Those items which still remain classified as threat items are then subject to investigation by the confirmatory sensor, 2509, 2609.

If the confirmatory sensor, 2509, 2609 clears an item, it is returned back to the main sorting loop, 2505, 2605 and continues its journey to its ultimate destination. In the event that the confirmatory sensor, 2509, 2609 confirms a threat baggage or cargo item, the item is passed through a divert point 2619 to a holding room 2613 where the baggage or cargo item can be reconciled with the passenger or owner of the item and subsequently hand searched by the appropriate authorities.

X-ray systems detect explosive devices and materials with a high degree of confidence, but generally cause a false alarm rate on typically between 10% and 30% of all the baggage and cargo items that have been inspected. These reject items are viewed by one or more operators who typically are able to resolve between 90% and 99% of all the threats identified by the automatic explosives detection algorithms in the X-ray system. Therefore, the remaining items are those that need to be scanned by the confirmatory sensor.

Accordingly, for a baggage or cargo line with 1800 items per hour at the input, in one embodiment, up to 600 items per hour may be identified as potential threat items by the automatic explosives detection algorithms of the X-ray system and designated for visual inspection. Of these, up to 60 items per hour may be marked as being a potential threat by the inspectors. In another embodiment, as few as 180 items per hour may be identified as potential threat items by the X-ray system automatic explosives detection algorithms and designated for visual inspection. Of these, up to 2 items per hour may be marked as being a potential threat by the inspectors following visual inspection.

Therefore, the secondary, confirmatory sensor should be designed to take only a few minutes to complete its analysis and confirm the nature of the materials identified in the baggage or cargo item. This will allow unimpeded flow of baggage and cargo items through the system with no more than a few minutes delay for any baggage or cargo item for the purposes of high integrity security screening. Accordingly, the present invention employs high throughput embodiments of the secondary confirmatory system.

Confirmatory Sensor Embodiment One Nuclear Quadrupole Resonance (NQR)

In one embodiment, the confirmatory sensor comprises a system for conducting a nuclear quadrupole resonance (NQR) measurement. Here, it is known that certain nuclei, in particular nitrogen and chlorine, possess a significant magnetic quadruple moment. Normally, the magnetic quadrupole moments of the individual spinning nuclei in a sample of material are aligned in random orientations. Under the application of a strong applied magnetic field, the individual magnetic quadrupole moments of the nuclei in the material under inspection line up with the applied magnetic field, thereby forming a weak magnetic field acting in the opposite orientation to the applied field. An applied field may be in the range of 10 to 100 milli Tesla while the generated field due to the aligned nuclei may be only in the fempto Tesla range. Once the applied magnetic field is switched off, the magnetic dipoles begin to move out of alignment and the magnitude of the combined magnetic field starts to the reduce.

The strength of the magnetic field in the first place depends on the type of nuclei and the concentration of these nuclei in the material under investigation. The rate at which the field due to the nuclei builds up under the influence of the applied magnetic field and how it dissipates again once the applied magnetic field is removed is dependent on the local chemical environment and lattice structure of the nuclei within the material under investigation.

Due to the small size of the magnetic field that is generated due to alignment of nuclei in the sample of interest by the applied magnetic field, measurement of signal due to the generated field is generally noisy. Therefore, in order to build up the signal-to-noise ratio in the measurement it is advantageous to repeat the measurement many times and to process the signals following each applied field stimulus into one collective signal.

Figure 27:
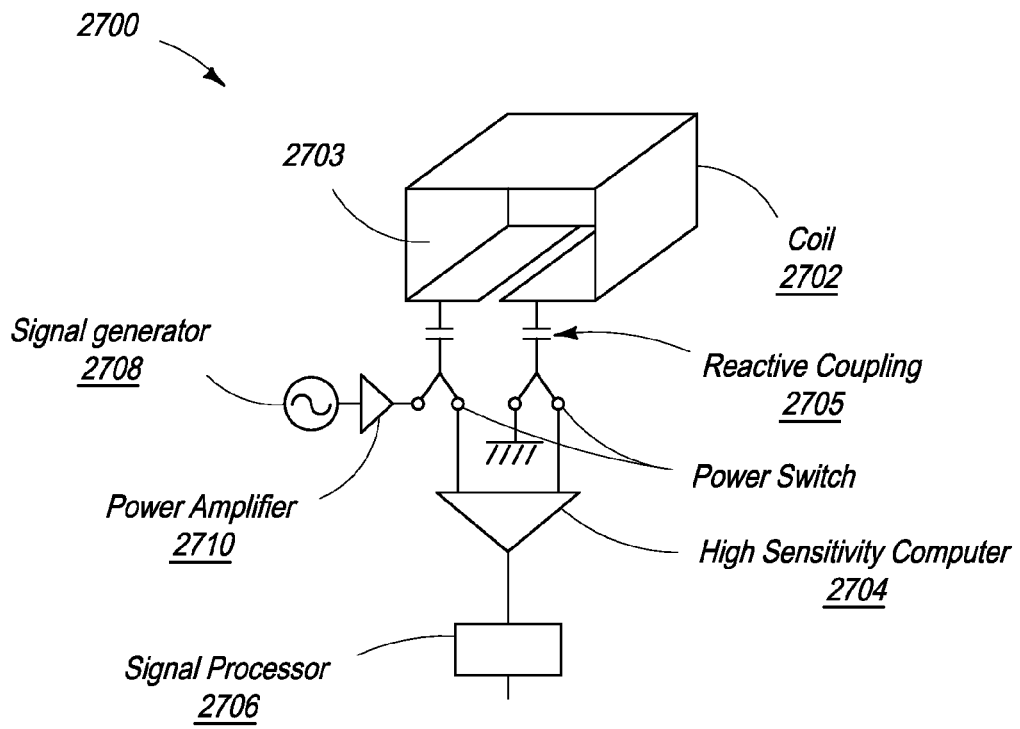
FIG. 27 is one embodiment of a confirmatory sensor comprising a NQR detection system.

Referring to FIG. 27, a stimulating coil and associated electronics for a NQR confirmatory sensor 2700 is shown. Here, the coil 2702 is shown as a single turn which extends to a suitable distance such that the item to be inspected can be contained within the three dimensional envelope of the coil, defined as the internal region 2703. Preferably, the coil 2702 is fabricated from a material with low resistivity to simplify tuning the resonant circuit of the coil and to reduce electrical power dissipation in the coil 2702 which can result in unwanted thermal heating. A suitable coil material is copper.

A signal generator 2708, preferably a digitally programmable signal generator, is used to drive the coil 2702 via a power amplifier 2710 with suitable bandwidth, typically being up to 10 MHz. Preferably, the power amplifier 2710 drives the coil 2702 through a fast acting power switch 2705. This power switch 2705 provides isolation between the high current applied magnetic field and the sensitive amplifier 2704 which is used to detect the resulting magnetic signal from the material under inspection.

A high gain, high sensitivity, amplifier 2704 is connected via the reactive coupling components 2705 to the coil 2705 used to stimulate the material. This amplifier 2704 is typically designed to reject common mode signals and those ambient signals which are not in the frequency range of interest from its analog output signal. A following signal processor unit 2706 digitises the analog signal from the high gain amplifier 2704 and applies suitable digital filtering, such as fitting exponentially decaying functions to the envelope of the detected signal. The system determines the relaxation times of the induced magnetic quadrupole signals. These relaxation times are dependent on both the nucleus itself and on the chemical environment and lattice structure in which the nucleus is situated.

Figure 28A:
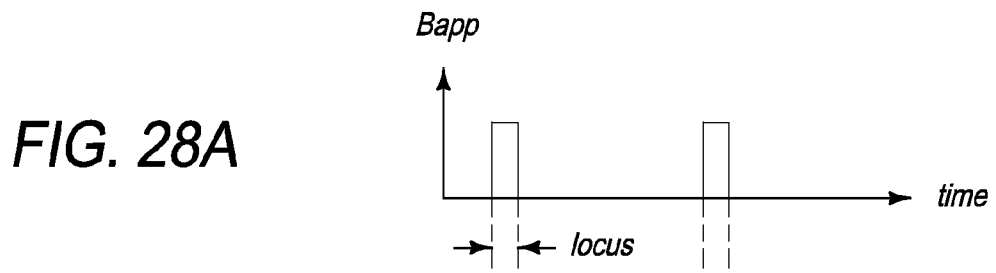
FIG. 28a is a first exemplary graph of a pulse sequence for an NQR detection system.
Figure 28B:
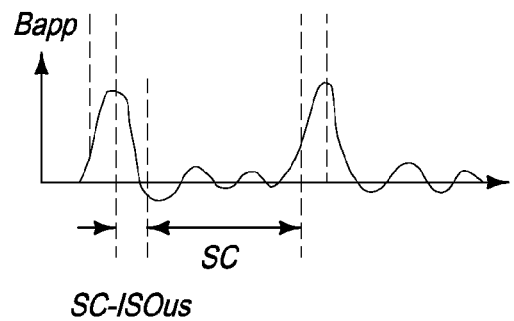
FIG. 28b is a second exemplary graph of a pulse sequence for an NQR detection system.

The applied magnetic field is typically pulsed with a predetermined pulse sequence to maximise the induced signal and to provide time between pulses for the induced signal to be recorded and the signals processed as appropriate. FIGS. 28*a* and 28*b* show an exemplary pulse sequence for the applied signal and the output, respectively. Referring to FIG. 28*a*, The applied signal is typically asserted on the order of 400 microseconds. This provides time for the signal to build close to its saturation level. Once the applied stimulus is removed, a short dead time follows (typically 50 to 150 microseconds) for residual eddy currents in the coil to disappear prior to signal acquisition, as shown in FIG. 28b. The output signal is usually timed over a 500 to 1000 microsecond period. The period of the pulse sequence is thus typically in the range 200 Hz to 2 kHz. In order to provide a good level of explosives detection, a total measurement time of between 1 and 5 seconds is usually employed.

The pulse sequence and associated digital filtering is designed specifically for each type of explosive material that may be of interest. Therefore, if a set of four or five compounds is to be searched, the total measurement time may extend out to 30 seconds.

Since in this combined system, the X-ray data will already provide a-priori estimation of the type of explosive material that may be present, the nuclear quadrupole measurement is targeted first to the anticipated explosive material, and if no match is found, related compounds can be screened. This helps to minimise the examination time which is advantageous.

The baggage or cargo item to be inspected is advantageously passed into the scanning area through a conductive tunnel whose dimension is substantially smaller than the coil size in order to provide good immunity from ambient electromagnetic noise sources.

Confirmatory Sensor Embodiment Two: X-Ray Diffraction

In another embodiment, the confirmatory sensor comprises an X-ray diffraction system. X-rays in the energy range of 10 keV to 200 keV possess an associated wavelength which is commensurate with that of the lattice spacing in known materials. The wavelength of a 10 keV X-ray is $1.24 \times 10^{-10}$ m (1.24 Angstom) while that of a 200 keV X-ray is $6 \times 10^{-12}$ m (0.06 Angstrom). In the situation where the wavelength of a wave and the spacing of scattering objects through which the wave is propagating is similar to the wavelength, then diffraction of the wave will occur according to the Bragg scattering condition $$n\lambda = 2d \sin \theta$$

where n=order of the diffraction pattern, $\lambda$=wavelength of the wave, d=lattice spacing and $\theta$=diffraction angle.

In the case of X-rays, Bragg scattering may be used to determine lattice spacing and hence confirm the material type. In a practical X-ray system, the X-ray source produces not just one energy but a plurality of energies, typically in the energy range from 10 keV up to the maximum accelerating voltage placed on the tube and generally up to 200 keV. These energies are dispersed over the whole energy range, some energies being more likely than others.

Figure 29:
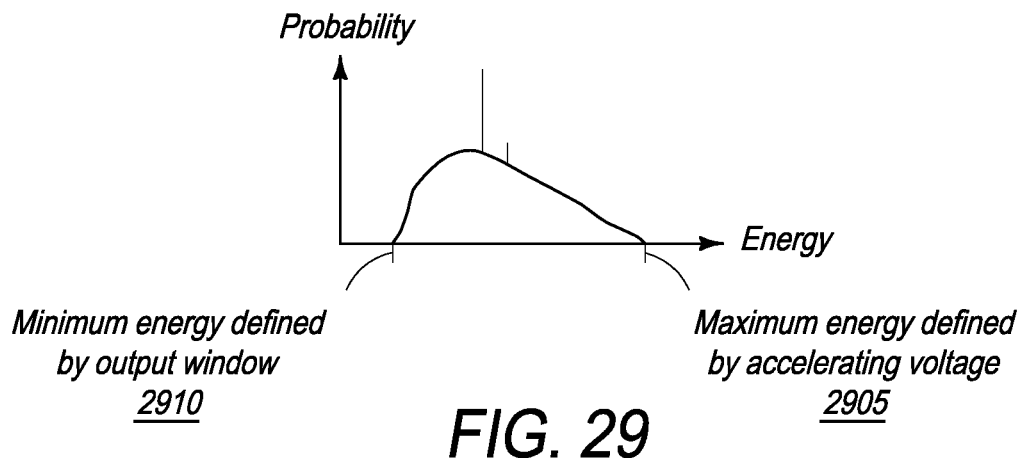
FIG. 29 is an example X-ray spectrum from a standard X-ray tube.

FIG. 29 provides an example X-ray spectrum from a standard X-ray tube. Here, the maximum X-ray energy 2905 is defined by the accelerating voltage that is applied to the X-ray tube. If the tube is operated with an accelerating voltage of 160 kV, then the maximum possible X-ray energy is 160 keV. The most likely X-ray energy is of course much lower than this. The minimum X-ray energy 2910 is theoretically close to zero, but in reality the minimum X-ray energy is defined by the material type and thickness of the vacuum support window through which the X-ray beam propagates from the X-ray target to the object under inspection.

Figure 30A:
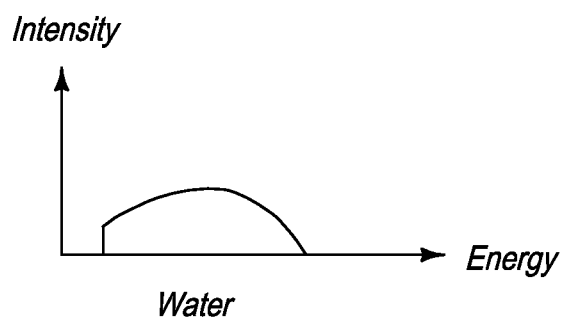
FIG. 30a is a first exemplary indicative X-ray diffraction spectra for an amorphous material like water and a polycrystalline material such as an explosive.
Figure 30B:
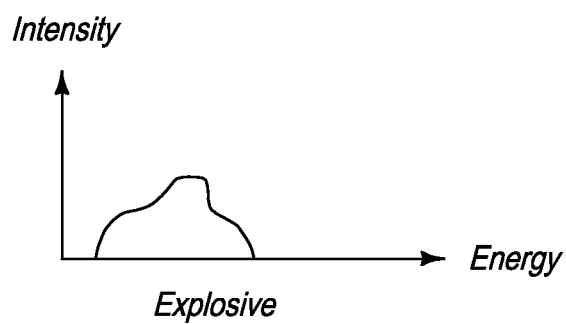
FIG. 30b is a second exemplary indicative X-ray diffraction spectra for an amorphous material like water and a polycrystalline material such as an explosive.

If the material under inspection comprises just a single lattice parameter then it may be seen that different diffraction spectra will be generated for all components of the X-ray spectrum. The net effect is of a broad diffraction peak compared to the case where a mono-energetic X-ray source is used. Similarly, a real material is generally polycrystalline or even amorphous in which case further broadening of the diffraction spectra will occur. Nonetheless, empirical measurement of diffraction spectra intensity and energy can provide very good materials characterization for even similar materials. Indicative X-ray diffraction spectra for an amorphous material like water and a polycrystalline material such as an explosive are provided for reference in FIGS. 30a and 30b, respectively.

Figure 31:
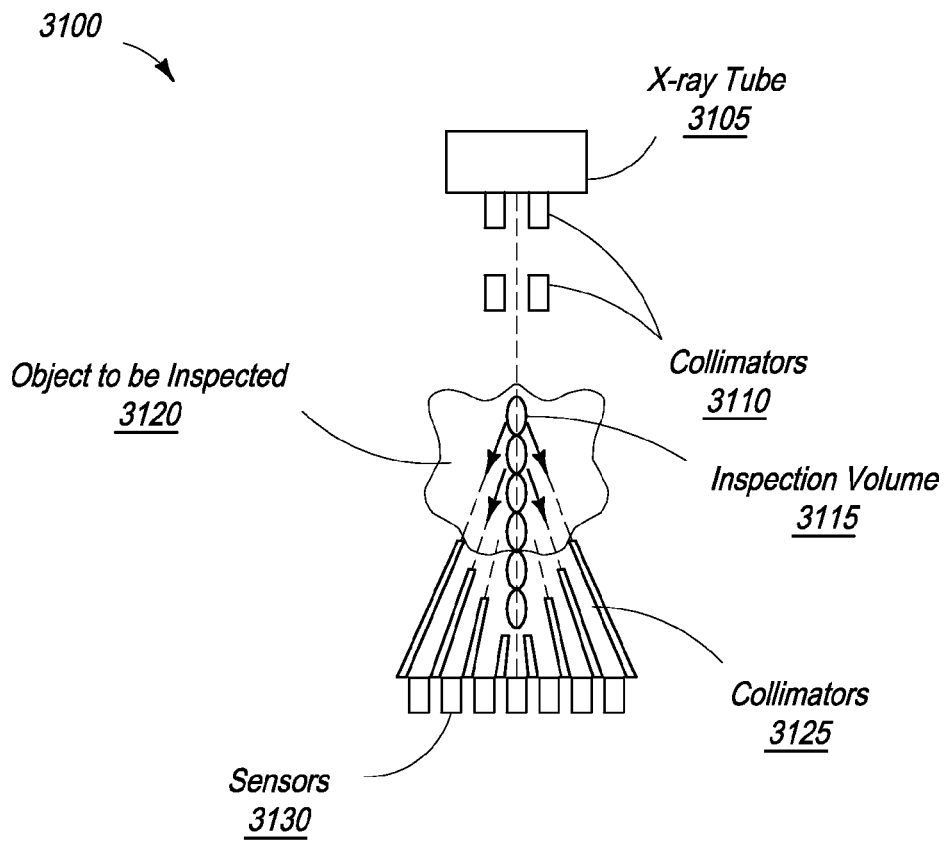
FIG. 31 is an exemplary embodiment of an X-ray diffraction system for use as a confirmation sensor.

An exemplary embodiment of an X-ray diffraction system for use as a confirmation sensor with a high speed electronically scanned X-ray tomography imaging system is provided in FIG. 31. Here, an X-ray beam emitted from an X-ray tube 3105 is collimated via collimators 3110 into a beam of rectangular or circular cross section, typically in the range 1 mm to 50 mm diameter. The smaller the beam, the more accurate the measurement is likely to be but the longer that the scan will take to complete. A set of detectors 3130 are located opposite to the source 3105 but on the opposite side of the object to be inspected 3120. Each detector 3130 is located behind secondary collimators 3125, the secondary collimators 3125 being designed to shield scattered radiation from all parts of the object under inspection 3120 except for a small volume where the collimated beam intersects with the primary beam volume. This intersecting region constitutes an inspection volume 3115 for that particular detector. Each detector 3130 has a specific secondary collimator 3125 design such that it interrogates a particular inspection volume 3115 along the length of the primary beam volume. Preferably, each collimated detector element 3130 is configured to sample a different part of the primary beam volume. In this way, parallel data acquisition can be achieved at all intersecting volumes between the object under inspection 3120 and the primary X-ray beam.

The secondary collimators 3125 and X-ray detectors 3130 are arranged in a linear configuration such that they each subtend substantially the same scattering angle to the axis of the primary beam. A suitable scattering angle is in the range of 3 degrees to 10 degrees, an optimal angle being typically 6 degrees.

Figure 32:
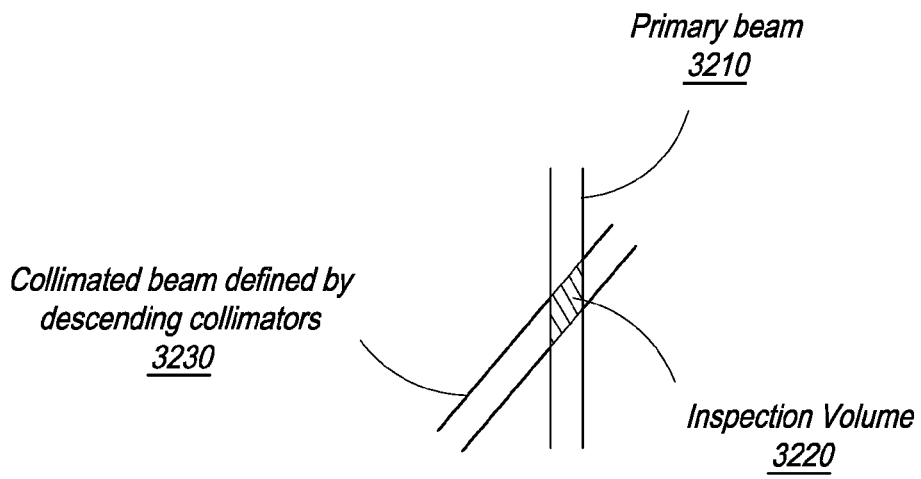
FIG. 32 is an inspection region defined by the intersection of a primary beam and a secondary collimator beam.

As shown in FIG. 32, the length of the inspection region 3220 described by the intersection of the primary beam 3210 and the secondary collimator beam 3230 is typically in the range from 10 mm to 100 mm and may advantageously be set at 50 mm as a compromise between detection efficiency, scanning time and system cost.

Figure 33:
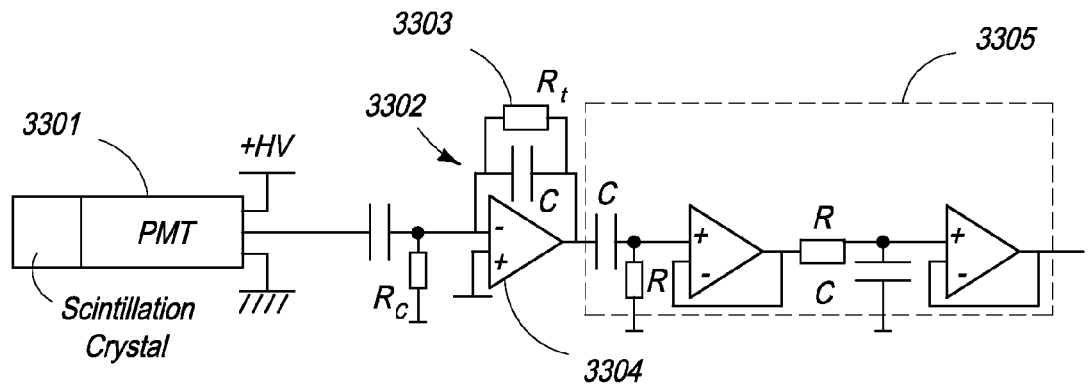
FIG. 33 depicts a detector coupled to a suitable readout circuit with pulse shaping capability.

The X-ray detectors advantageously provide a suitable energy resolution such that each detected X-ray can be assigned to a particular region of the measured X-ray spectrum at each detection point. A suitable detector is an inorganic scintillation crystal such as NaI(Tl) of CsI coupled to a suitable readout circuit with pulse shaping capability. An exemplary readout circuit is shown in FIG. 33 in which a photomultiplier tube 3301 converts the optical signal from the photomultiplier into an electronic signal. Capacitor Cf 3302 is selected to give a suitable gain, while resistance Rf 3303 is selected to give a suitable pulse duration, typically in the range 50 microseconds to 1000 microseconds. The output from this first stage amplifier 3304 is then passed through a pulse shaping network 3305 comprising a CR-RC filter with time constant typically in the range 0.1 microseconds to 2 microseconds, the precise value being selected to give acceptable count rate performance while maintaining a good noise performance. A 1 microsecond shaping time is generally preferred. The output from the circuit shown in FIG. 33 is passed to an analog-to-digital converter (not shown) and to a histogramming digital memory which builds up a pulse height spectrum. A typical scintillation crystal size is in the range 10 mm to 50 mm diameter with a thickness of up to 10 mm.

An alternate detector with improved energy resolution can be selected from the semiconductor detectors, in particular hyper pure germanium which is preferably operated at the temperature of liquid nitrogen (77 K) or CdZnWO4 which is commonly operated at room temperature. Semiconductor detectors tend to be more expensive to use and exhibit some additional complexity in operation, such as the need to use liquid nitrogen.

Once a spectrum from a particular point in the inspection volume has been accumulated, this information can be compared to a database of empirically derived reference spectra by, for example, using a least squares fit of the measured spectrum normalized to a set of reference spectra. Once a fit is determined that is within a certain threshold value, it may be understood that differences between the two spectral shapes are minimal and therefore it is possible to conclude that an explosive material is likely present.

In a practical embodiment of this invention, the high speed X-ray system provides a high degree of information on the location and shape of the anticipated threat material. The X-ray diffraction system is analyzing substantially along a certain line through the object. It is therefore recognized that the three-dimensional X-ray image data may be used to target the most appropriate trajectory of the X-ray diffraction system beam through the object to be inspected.

In one embodiment, the image data from the X-ray tomography system is used to reconstruct a three-dimensional set of surfaces that accurately define the exterior shape of the object to be inspected. Once the object to be inspected arrives at the X-ray diffraction confirmatory sensor, the bag orientation will not be the same as when the X-ray image data was collected. Therefore, the X-ray diffraction system is provided with a series of video cameras 3401, as shown in FIG. 34, which together can be used to reconstruct a three-dimensional outer surface for the object to be inspected.

Using the three-dimensional image of the object exterior calculated by the X-ray tomography and that calculated by the video cameras, a three-dimensional matrix may be calculated which describes the relative orientation of the object between the two detection systems. Given the high spatial resolution of the three-dimensional X-ray tomography image, an optimal path for the X-ray diffraction beam through the object to be inspected may be calculated. Since the matrix which describes the relative orientation of the bag in the two inspection systems is known, then given a manoeuvrable diffraction probe, it is possible to set the diffraction beam to pass along the most optimal path through the object.

For example, known diffraction sensors can find it difficult to detect explosive materials in configurations where they are small in one dimension compared to another. In the present invention, the X-ray beam may be targeted to most optimally interrogate the object based on a-priori information from the three-dimensional X-ray tomography image.

Figure 34:
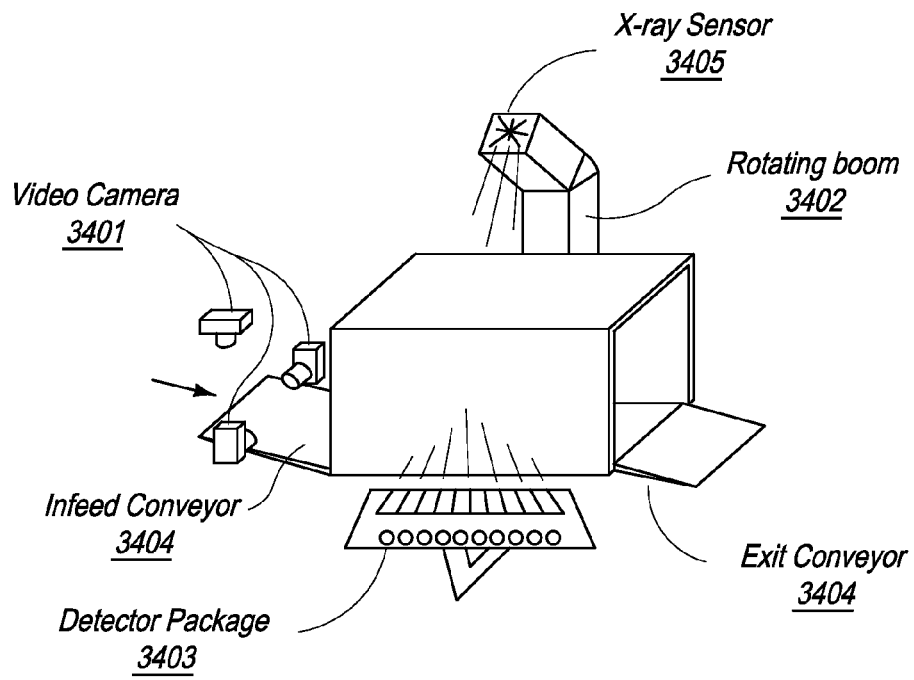
FIG. 34 depicts a diffraction detection package arranged to lie substantially parallel to the direction of conveyor motion.

Referring to FIG. 34, a rigid but moveable boom 3402 is provided to allow motion of the X-ray sensor and X-ray tube in two dimensions. As shown in FIG. 34, the diffraction detection package 3403 is arranged to lie substantially parallel to the direction of motion of the conveyor 3404. In one embodiment, the detection package is 200 mm to 1200 mm long and still fits in a compact equipment footprint. This is important for use of the equipment in space constrained environments like an airport baggage hall. The X-ray source 3405 and its associated collimators (not shown) are fixed to the same rigid but moveable boom such that the relationship between the detector package 3403, the X-ray source 3405 and its collimators remains fixed independent on the position of the boom.

Figure 35:
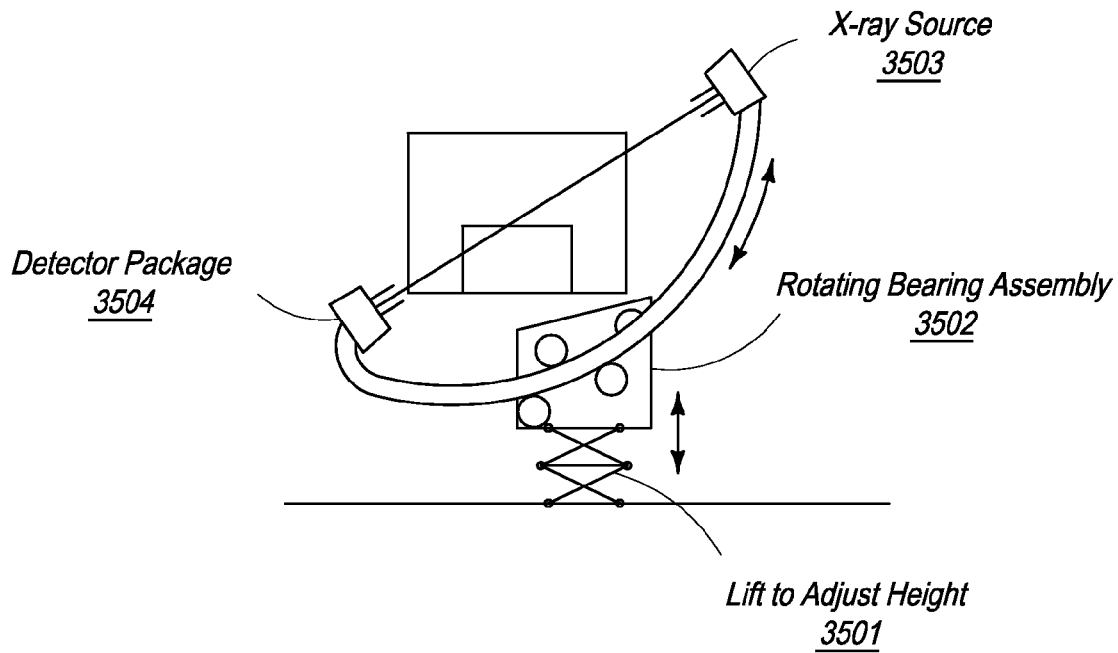
FIG. 35 depicts a boom fixed to a control system that allows the diffraction beam to be rotated from a substantially vertical orientation to a substantially horizontal orientation.

Referring to FIG. 35, the boom is fixed to a control system that allows the diffraction beam to be rotated from a substantially vertical orientation to a substantially horizontal orientation. Further, the control system allows the boom to be shifted up and down in the vertical direction. This control system comprises a lift 3501 for adjusting the height and a rotating bearing assembly 3502 to provide the desired motion of the beam between the X-ray source 3503 and the detector package 3504. One of ordinary skill in the art would appreciate that the layout provided in the drawing is an example only, and other boom and control system configurations can be adopted to achieve the same result.

Given this beam steering configuration, the optimized beam path is calculated by interrogating the three-dimensional X-ray tomography image with a set of beams that have been transformed from the X-ray diffraction system frame of reference using the matrix determined by video analysis of the object outline. Once an optimal beam trajectory has been calculated, the X-ray diffraction probe is adjusted into the appropriate position and the object moved using the conveyor until the optimal scan line has been achieved. At this point the X-ray beam is switched on and the data collection period starts. After a suitable time, typically between 1 and 5 seconds, the X-ray diffraction signals are compared with known reference spectra. If a clear match is observed the scan can be terminated. If not, the beam is switched back on and the mechanical assembly is moved around the anticipated inspection point in the object under inspection by relatively small distances, typically by less than 100 mm in the vertical direction and up to 10 degrees in the rotation plane. The data is evaluated at all times during this process which may take up to several minutes. At the end of the inspection period, if no diffraction data is observed which matches a known threat, the scan is terminated and the baggage or cargo item under inspection is cleared for onward transit.

In a further embodiment of this invention, the tunnel surrounding the object under inspection forms the coil assembly for a nuclear quadrupole measurement system and the X-ray diffraction probe analyses the object through the coil assembly. The two sets of data, nuclear quadrupole resonance and X-ray diffraction, can be acquired simultaneously or sequentially as time permits.

Confirmatory Sensor Embodiment Three: X-Ray Backscatter Imaging

In another embodiment, the confirmatory sensor comprises an X-ray backscatter imaging system.

X-ray backscatter is produced when X-rays undergo a Compton interaction. Here, the scattered X-ray is left with less energy than it had before the collision, the difference in energy being delivered to an electron in the material under investigation. There is a good probability that the X-ray will be scattered back in the direction from which it came and this backscattered X-ray can be detected with one or more X-ray sensors located adjacent to the source of X-rays. The direction of the scattered X-rays is independent of the direction of the input beam and therefore there is only weak spatial correlation between the backscattered signal from a particular object and the backscatter signal detection signal.

It is therefore preferable to incorporate a collimator into the system, between the X-ray source and the object under investigation, which can produce a one-dimensional scanning pencil beam of X-rays. As this beam scans, the detector signal is correlated with the current beam position, thereby forming a one-dimensional image of the object under investigation. If the object is then scanned past the plane of the X-ray beam, and data from the X-ray detectors is also correlated with the scan rate of the conveyor, then a two-dimensional X-ray backscatter image of the object under inspection will be produced. An effective pencil beam width will be in the range from 1 mm to 10 mm and will preferably be set at 2 mm in order to provide a good balance between spatial resolution and signal-to-noise ratio. At a conveyor speed of 0.5 m/s an optimized system will use a chopper wheel with four collimation ports operating with a rotation speed of 60 revolutions per second.

X-rays are scattered preferentially by high atomic number materials but are also absorbed preferentially by high atomic number materials. Therefore, the backscatter signal is dominated by signals from low atomic number materials and can be used to see low atomic number materials close to the surface of the object closest to the X-ray source.

Figure 36:
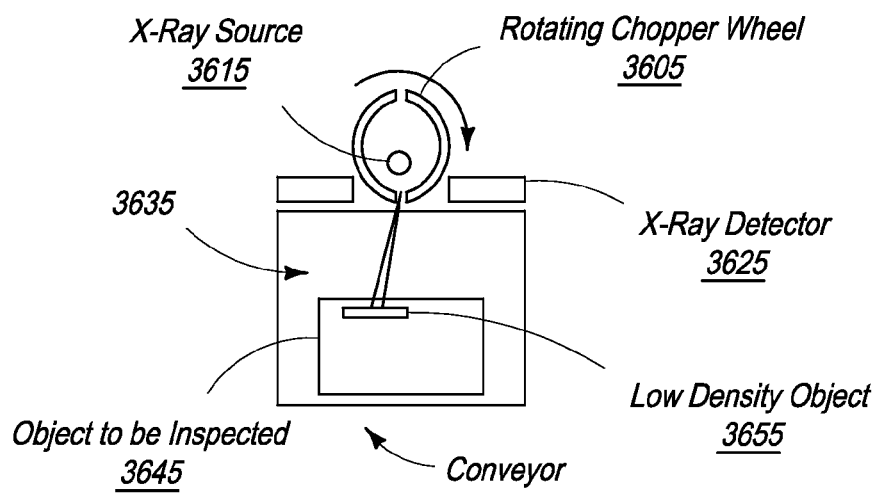
FIG. 36 depicts an exemplary backscatter system.

In one embodiment of this invention, referring to FIG. 36, a scanning wheel collimator 3605 provides a pencil beam of X-rays, by collimating X-ray emissions from an X-ray source 3615, which scans across the top surface 3655 of the baggage or cargo item being inspected 3645. X-rays 3635 which backscatter in the cargo are detected in adjacent X-ray detector blocks 3625. These detector blocks 3625 may be positioned at the end of the scanning region, or preferably they can be located parallel and adjacent to the scan line in an orientation 90 degrees rotated around from that shown in FIG. 36. As the baggage or cargo item 3645 is scanned, an image is formed which can be correlated with features that are located in the three-dimensional X-ray image.

It is preferable to match the orientation of the baggage or cargo item in the backscatter system to its orientation when it passed through the X-ray tomography scanner in order that the two sets of image data may be correlated. Although such a probe will not automatically confirm the presence of an explosive material, it may be used to provide confirmation of relative atomic number against the image generated by the X-ray tomography unit.

Confirmatory Sensor Embodiment Four: Trace Detection

In another embodiment, the confirmatory sensor comprises a trace chemical detector.

Certain explosive materials emit a chemical signature through vapour that emanates from the material at room temperature. This vapour may be present typically at parts per million to parts per billion in the air around a baggage or cargo item to be inspected. The actual concentration of signature molecules depends on the vapour pressure of the material itself as well as the rate of gas exchange between the baggage or cargo item to be inspected and the surrounding air. For example, a shrink-wrapped baggage item will reduce the exchange of gas between an explosive material within the baggage and the surrounding air.

Figure 37:
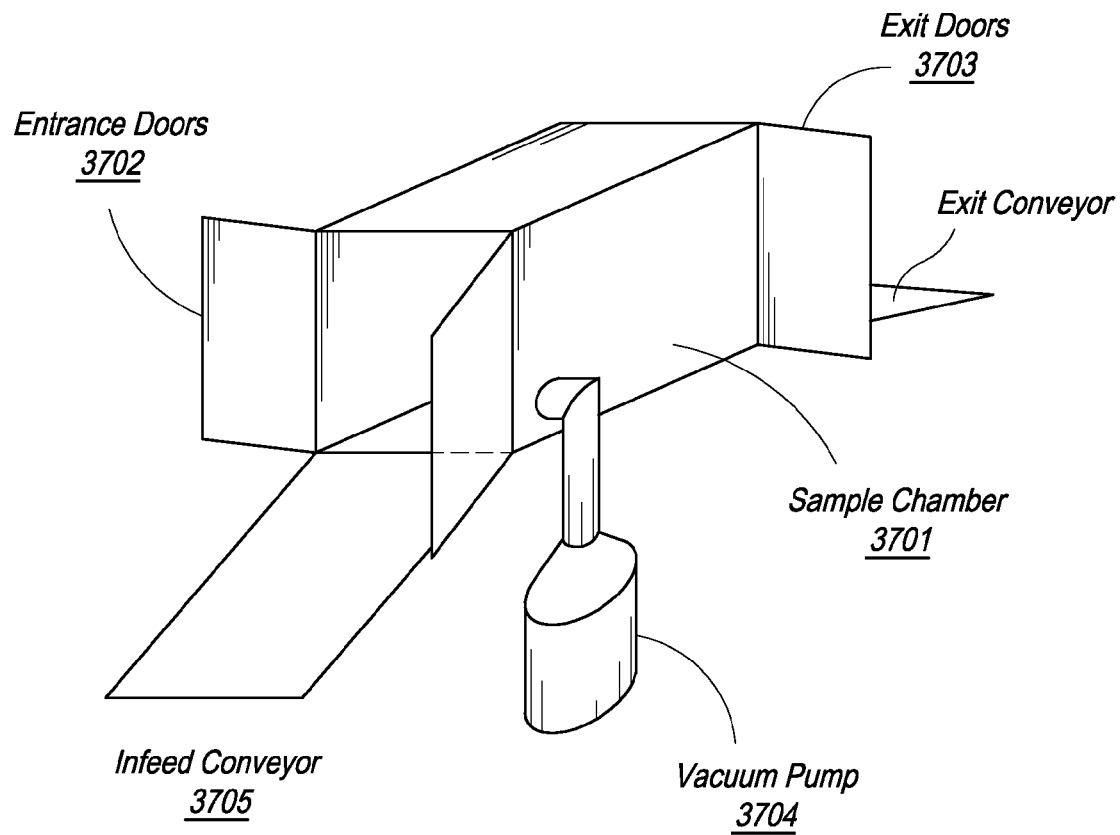
FIG. 37 depicts an exemplary trace detection system.

In one embodiment, the item to be inspected is passed into a chamber using a conveyor system. An exemplary chamber 3701 is shown in FIG. 37 with a conveyer 3705 passing through. Referring to FIG. 37, the chamber 3701 is sealed using a suitable mechanism such as doors 3702, 3703 that open and close to seal the entrance and exit ends of the chamber respectively, or shutters that drop down to close chamber. Attached to the chamber is a small vacuum pump 3704. The pump 3704 operates such that once the doors have been closed, the chamber 3701 can be brought down to a soft vacuum (typically in the range 50 to 100 mBar). At this point, trapped air and other gasses that have been in the baggage or cargo item are drawn out into the main chamber volume. One or more trace detection systems then analyze the residual gas in the chamber 3701 for the presence of explosive chemicals.

After the initial purge of air, the chamber is sealed to ensure vapour from the article under inspection remains within the chamber rather than being vented to atmosphere. After a suitable time, typically 10 seconds to 5 minutes, the signal analysis from the trace detection apparatus will be complete and can be correlated against the present of explosive materials that were predicted from the three-dimensional tomographic image system.

If a strong correlation is present, the baggage or cargo item can be marked as reject and passed to a reconciliation area as required. If an explosive material is identified that was not predicted by the X-ray system, the item can again be marked as reject. If no explosive material is identified by the trace detection system, a decision can be made to either hand search the baggage or to mark the item as cleared for onwards travel.

In a further aspect of this invention, the use of the trace detection equipment described here can be combined with the X-ray diffraction sensor system and/or the nuclear quadrupole resonance system. In one embodiment, up to three independent methods can be used simultaneously and in the same equipment for detection of explosive materials and devices. An algorithm may then be used to determine with what certainty a suspect item of baggage or cargo may be released for onwards travel. For example, each independent sensor can rank a unlawful object suspected during the first round of screening as 'Not Present', 'Possibly Present' and 'Definitely Present'. If one or more 'Definitely Present' measurements are obtained, the item should be restricted for onwards travel. If all sensors respond with 'Not Present', the item can be cleared for onwards travel. If two or more sensors respond with 'Possibly Present', the item should be restricted from onwards travel, and so on. Such a voting system provides a high degree of certainty in deciding the release of suspect baggage and cargo items for onward travel.

It shall be clear to those of moderate skill in the art that such a multi-layered approach using identical sensors, but with an expanded database, can be used in exactly the same way for the detection of contraband such as narcotics, tobacco products and currency, besides threat materials.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method for identifying objects in a container, comprising:
    performing a first stage screening, comprising: arranging a stationary X-ray source to generate X-rays from a plurality of stationary X-ray source positions around a scanning region, arranging a first set of detectors to detect X-rays transmitted through the scanning region, arranging a second set of detectors to detect X-rays scattered within the scanning region, and activating each of said plurality of stationary X-ray source positions in a sequence and rate to emulate an angular velocity of source rotation sufficient to generate data from which at least one tomographic image is formed;
    processing data output from the first set of detectors using at least one processor to generate the at least one tomographic image;

processing data output from the second set of detectors to generate scatter image data; and, performing a second stage screening comprising at least one of a NQR-based screening process, X-ray diffraction based screening process, X-ray backscatter based screening process, or trace detection based screening process.

2. The method of claim 1 wherein the at least one processor outputs data indicative of a suspect object in the container.

3. The method of claim 1 wherein the at least one processor outputs a signal indicating said container should be subject to the second stage screening only if the first stage screening identifies a suspect object in the container.

4. The method of claim 1 wherein the at least one processor outputs a signal indicating said container should not be subject to the second stage screening only if the first stage screening does not identify a suspect object in the container.

5. The method of claim 1 wherein the second stage screening outputs a signal indicative of whether a suspect object exists in the container and wherein said output of the second stage screening, said at least one tomographic image, and said scatter image data are used to determine if the suspect object is illegal.

6. The method of claim 1 wherein said first stage screening is performed in parallel with said second stage screening.

7. The method of claim 1 wherein said first stage screening is performed serially with respect to said second stage screening.

8. The method of claim 1 wherein the first stage screening is used to analyze at least one of the tomographic image data or scatter image data to determine a type of material of an object in the enclosure.

9. The method of claim 8 wherein the second stage screening is used to conduct a nuclear quadrupole measurement based on the type of material determined by the first screening system.

10. The method of claim 1 wherein the second stage screening is used to conduct an X-ray diffraction based screening based on the at least one tomographic image generated by the first stage screening.

11. The method of claim 1 wherein said stationary X-ray source is an electronically scanned X-ray source.

12. A method for identifying objects in a container, comprising:

performing a first stage screening comprising: arranging a stationary X-ray source to generate X-rays from a plurality of stationary X-ray source positions around a scanning region;

arranging a first set of detectors to detect X-rays transmitted through the scanning region;

activating each of said plurality of stationary X-ray source positions in a sequence and rate to emulate an angular velocity of source rotation sufficient to generate data from which at least one tomographic image is formed;

processing data output from the first set of detectors to generate the at least one tomographic image, using at least one processor; and conveying said container from a first stage screening area to a second stage screening area, wherein the second stage screening comprises at least one of a NQR-based screening process, X-ray diffraction based screening process, X-ray back-scatter based screening process, or trace detection based screening process.

13. The method of claim 12 wherein the at least one processor outputs data indicative of a suspect object in the container.

14. The method of claim 12 wherein the at least one processor outputs a signal indicating said container should be subject to the second stage screening only if the first stage screening identifies a suspect object in the container.

15. The system of claim 12 wherein the second screening system outputs a signal indicative of whether a suspect object exists in the container and wherein said output of the second stage screening and said at least one tomographic image are used to determine if the suspect object is a threat.

16. The system of claim 12 wherein said first stage screening is performed in parallel with said second stage screening.

17. The system of claim 12 wherein said first stage screening is performed serially with respect to said second stage screening.

18. The system of claim 12 wherein the first stage screening is used to analyze the tomographic image data to determine a type of material of an object in the enclosure.

19. The system of claim 18 wherein the second stage screening is used to conduct a nuclear quadrupole measurement based on the type of material determined by the first stage screening.

20. The system of claim 12 wherein the second stage screening system is used to conduct an X-ray diffraction based screening based on the at least one tomographic image generated by the first stage screening.

* * * * *